United States Patent
Choi et al.

(10) Patent No.: US 6,793,789 B2
(45) Date of Patent: Sep. 21, 2004

(54) REFERENCE ELECTRODE WITH A POLYMERIC REFERENCE ELECTRODE MEMBRANE

(75) Inventors: Yong Suk Choi, Seoul (KR); Sung Dong Lee, Youngchon-si (KR); Seong Hee Oh, Seoul (KR); Hyo Lin Lee, Kwachun-si (KR); Jae Ho Shin, Seoul (KR); Jeonghan Ha, Kyungsangnam-do (KR); Hakhyun Nam, Seoul (KR); Geun Sig Cha, Seoul (KR)

(73) Assignee: Geun Sig Cha, Seoul (KR)

(*) Notice: Subject to any disclaimer, the term of this patent is extended or adjusted under 35 U.S.C. 154(b) by 174 days.

(21) Appl. No.: 09/960,432

(22) Filed: Sep. 22, 2001

(65) Prior Publication Data

US 2002/0065332 A1 May 30, 2002

(30) Foreign Application Priority Data

Sep. 30, 2000 (KR) .......................... 2000-57640
Jun. 13, 2001 (KR) .......................... 2001-33085

(51) Int. Cl.$^7$ .............................................. G01N 27/31
(52) U.S. Cl. ........................................ 204/435; 204/418
(58) Field of Search ................................ 204/435, 416, 204/418, 419

(56) References Cited

U.S. PATENT DOCUMENTS

| | | | | |
|---|---|---|---|---|
| 3,691,047 A | * | 9/1972 | Ross et al. | |
| 4,214,968 A | * | 7/1980 | Battaglia et al. | |
| 4,781,907 A | * | 11/1988 | McNeill | 423/351 |
| 5,958,201 A | * | 9/1999 | Craig et al. | |
| 6,214,185 B1 | * | 4/2001 | Offenbacher et al. | 435/4 |
| 6,416,646 B2 | * | 7/2002 | Chan | 205/789 |

OTHER PUBLICATIONS

An article entitled "Promising New Solid–State Reference Electrode", By K. Nagy et al., published by J. Electrochem. Soc., vol. 144, No. 1, Jan. 1997, pp. L1–L2.

An article entitled "Fabrication and Characterization of a Solid State Reference . . . ,", By Melissa A. Nolan et al., published by Analytical Chemistry, vol. 69, No. 6, Mar. 15, 1997, pp. 1244–1247.

An article entitled "Thick film silver–silver chloride reference electrodes", By A. W. J. Cranny et al., published by Meas. Sci. Technol., vol. 9 (1998) pp. 1557–1565.

* cited by examiner

Primary Examiner—Kaj K. Olsen
(74) Attorney, Agent, or Firm—Bachman & LaPointe, P.C.

(57) ABSTRACT

Disclosed is a polymeric reference electrode membrane comprising (a) one selected from a porous polymer or a hydrophilic plasticizer; (b) a lipophilic polymer; and optionally an adhesion-enhancing material. A reference electrode equipped with the polymeric reference electrode membrane can be shortened the preconditioning time, and extended lifetime for storage and use owing to excellent adhesion, and showed reproducibility and good yield. So, a miniaturized multi-potentiometric sensor can be fabricated comprising a solid-state reference electrode of the present invention and a set of ion-selective electrodes, thus being useful in the potentiometric fields, including clinical, environmental, food and industrial analysis.

25 Claims, 17 Drawing Sheets

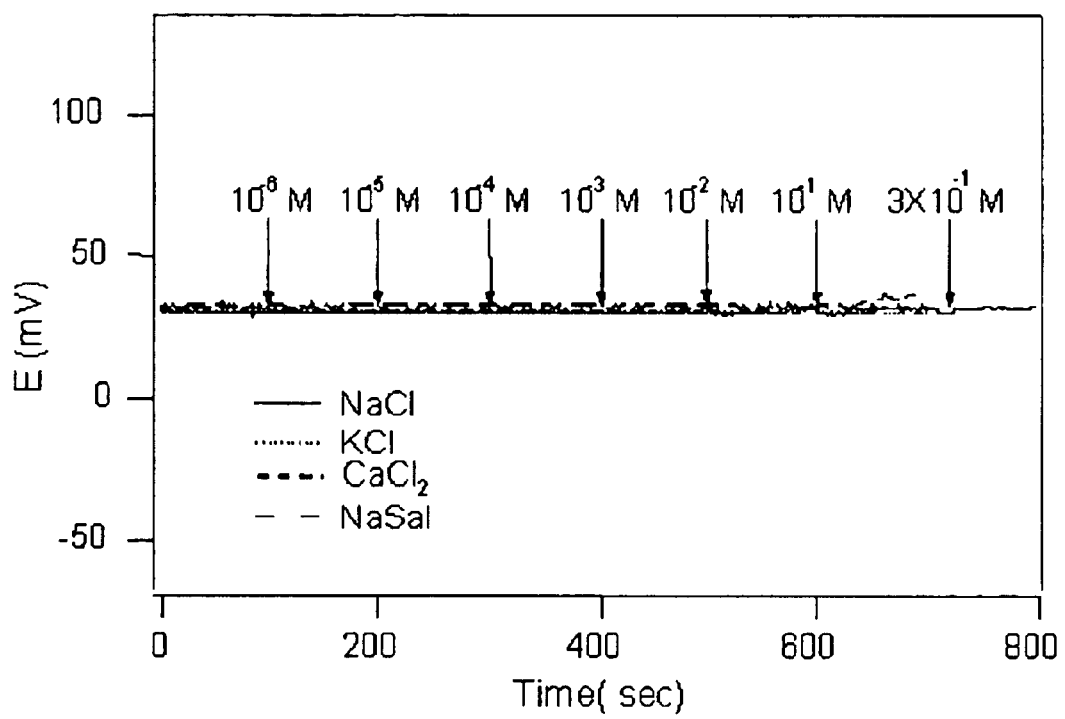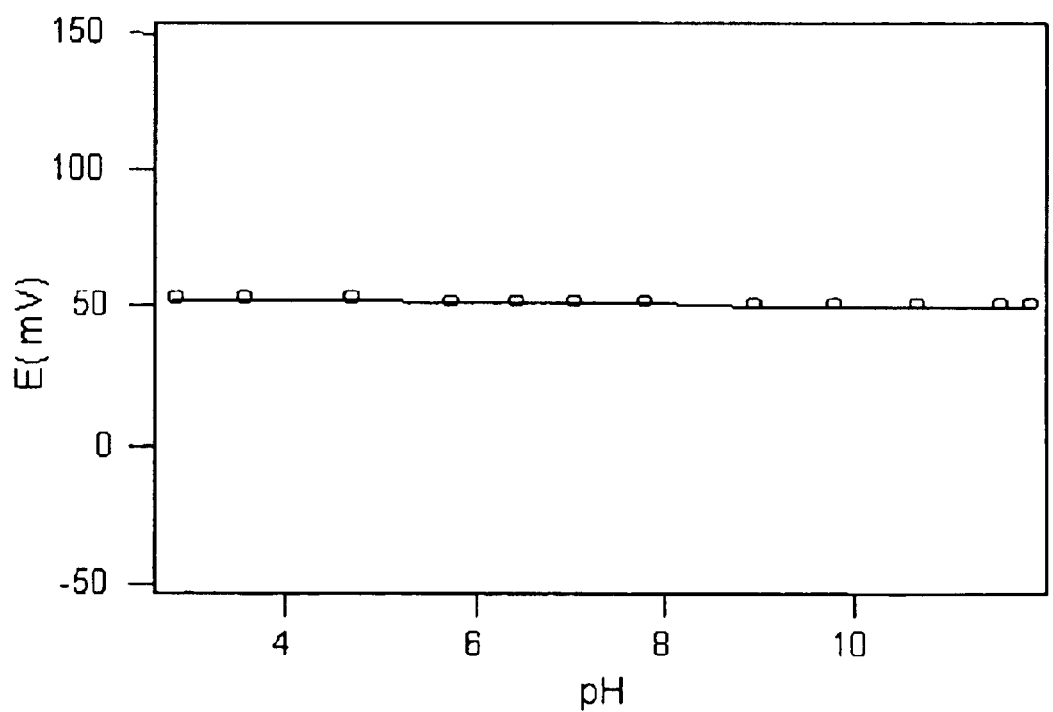

REFERENCE ELECTRODE WITH A POLYMERIC REFERENCE ELECTRODE MEMBRANE

FIELD OF THE INVENTION

The present invention relates to a polymeric reference electrode membrane, which comprises (a) one selected from a porous polymer or a hydrophilic plasticizer; (b) a lipophilic polymer; and optionally an adhesion-enhancing material, and a conventional-type reference electrode and a solid-state reference electrode equipped with the polymeric reference electrode membrane. Further, the present invention is concerned with a miniaturized multi-potentiometric sensor comprising a solid-state reference electrode and a set of ion-selective electrode.

BACKGROUND OF THE INVENTION

Potentiometry, as an electroanalytical chemistry, has been widely used in the determination of quantities of electrolytes in liquid samples in the fields of clinical, environmental, food and industrial analysis. However, when electrochemical analysis is performed in the laboratory, the sample may be contaminated or denatured due to the delay in sample transportation. In order to circumvent the problems, it is preferred that samples be analyzed at the spot. Particularly, medical analyzers that analyze clinical samples such as blood are necessary to use samples of as little volume as possible in order to minimize the patient's discomfort upon sampling, in addition to overcoming the analysis delay problems. Additionally, low prices are required for analyzers such that medical tests performed therewith can be universalized. In consequence, analyzers should be minimal in size, portable and inexpensive.

To minimize electrochemical analyzers is essential to reduce the dimensions of electrode systems. Generally, electrode systems are composed of a reference electrode and a working electrode. Compared with other components of electrode systems, more effort has gone into the miniaturization of a working electrode, so that practically various structures of practical working electrode have been developed. Meanwhile, the reference electrode is not advanced in size reduction, so that its large sizes make it difference to miniaturize electrochemical analyzer in miniaturizing Typically, electrochemical sensors have two-electrode system provided with working electrodes, which sensitively respond to species of interest, and reference electrodes, which maintain constant potentials without responding to the species. The working electrodes measure not values of absolute potentials, but values relative to the constant potential of the reference electrodes, that is, potential differences.

In electrochemical analysis, therefore, reference electrodes must maintain constant potentials irrespective of surrounding conditions and return instantaneously to initial equilibrium potentials after a current flow. Reference electrodes containing insoluble metal salts such as Ag/AgCl, are not dissolved in electrolytes. Another requirement for a reference electrode should be a short preconditioning time thereby being available to achieve point-of-care. Of course, high reproducibility is essential for making reference electrodes reliable.

As an effort to develop a planar-type small solid-state reference electrode suitable for use in electrochemical measurement, a reference electrode is reported that a layer of potassium chloride-dissolved glass paste having low melting point or a layer of thermosetting silicone polymer paste is formed on a silver/silver chloride layer coated through a screen printing method, and then a hydrophobic polymer insulating paste is overlaid onto the paste layer. (Cranny, A. W. J. and Atkinson, J. K. *Meas. Sci. Technol.* 1998, 9, 1557–1565). When the polymer insulating paste is overlaid, small hydration holes should be in the insulating paste to allow the diffusion of potassium chloride-dissolved paste layer to aqueous solution. Such reference electrode has long use lifetime, but it takes about 1 hour or more for preconditioning the electrode.

As an example of another type of solid-state reference electrode, it is reported that potential difference is offset between an anion-selective electrode and a cation-selective electrode (Nagy, K; Eine, K; Syverud, K; Aune, O. *J. Electrochem. Soc.* 1997, 144, L1–L2). In the reference electrode structure, the anode-selective membrane comprises a support, a plasticizer, an anionic lipophilic additive, and an anion exchange membrane, while the cation-selective membrane comprises a support, a plasticizer, a cationic lipophilic additive, and a cation exchange membrane.

The reference electrode requires long preconditioning time, and its use may be restricted until an anion-selective electrode and a cation-selective electrode are simultaneously activated, because the method needs to offset the potential difference between them. The reference electrode can offset the sensing of cations and anions having the same charge number, but cannot function owing to a potential difference attributable to the sensing difference between ion-selective membrane electrodes for ion species having different charge number and mixed ion species.

Another example of a small solid-state reference electrode, ultramicroelectrodes have been proposed, suitable for square wave anodic stripping voltammetry using an anion exchange membrane, Nafion, or polymers such as polyurethane (Melissa A. Nolan; Sandie H. Tan; Samuel P. Kounaves. *Anal. Chem.* 1997, 69, 1244–1247).

The ultramicroelectrode is fabricated that silver/silver chloride is immersed in sodium chloride (NaCl)/poly (vinyl chloride) solution, and coated with salt, followed by coating with Nafion or polyurethane. In square wave anodic stripping voltammetry, chloride ions present in samples react with metal ions to form a complex, so it is important to block inflow of chloride ions. Nafion introduced to the reference electrode acts as an anion exchange membrane and thus is responsible for preventing the chloride ion from being introduced into the samples. However, Nafion used for the anion exchange membrane of the reference electrode suffers from poor adhesion, long preconditioning time, noise, and too high sensitivity to ions, and thus cannot be applied to potentiometric measurement system.

In addition, a reference field effect transistor based on perchlorate, and fluoride ion-selective field effect transistor, as other small solid-state reference electrode, is reported (Potter W.; Dumschat, C.; Cammann K. *Anal. Chem.* 1995, 67, 4586–4588). The reference field effect transistor based on perchlorate ion-selective field effect transistor can be easily miniaturized, but cannot be applied to voltammetry because of the high resistance of the reference field effect transistor itself and sensing to electrolyte of high concentration. Also, instability of the ion-selective field effect transistor itself causes necessarily to a flow potential of the reference field effect transistor, which is a reference electrode of the ion-selective field effect transistor.

Meanwhile, the reference field effect transistor based on fluoride ion-selective field effect transistor containing a polymeric membrane capable of reducing a diffusion of calcium fluoride, its inner electrolyte, is affected by not only concentrations of fluoride ions and calcium ions in the samples but also interfacial contact potential between the inner electrolyte and the sample, due to low solubility of calcium fluoride.

SUMMARY OF THE INVENTION

Leading to the present invention, the intensive and thorough research on polymeric reference electrode membranes, conducted by the present inventors aiming to overcome the problems encountered in prior arts, resulted in the finding that, when a polymeric reference electrode membrane comprises (a) one selected from a porous polymer or a hydrophilic plasticizer; (b) a lipophilic polymer; and optionally an adhesion-enhancing material, the membrane can allow short preconditioning time required for sample analysis whereby improving reproducibility and yield due to excellent adhesion of the membrane to solid substrate, and maintain stable potential for mixed ion species and protein-containing calibration solutions, serum and whole bloods, thereby resulting in a miniaturized multi-potentiometric sensor having a solid-state reference electrode equipped with the polymeric reference electrode membrane.

Therefore, it is an object of the present invention to provide a polymeric reference electrode membrane comprising (a) one selected from a porous polymer or a hydrophilic plasticizer; (b) a lipophilic polymer; and optionally an adhesion-enhancing material.

It is another object of the present invention to provide a conventional-type reference electrode equipped with the polymeric reference electrode membrane.

It is further object of the present invention to provide a solid-state reference electrode, which characterizes a double layered or a mono-layered solid-state reference electrode, equipped with the polymeric reference electrode membrane.

It is a still further object of the present invention to provide a multi-potentiometric sensor comprising a reference electrode selected from a double layered or a mono-layered solid-state reference electrode and a set of ion-selective electrode.

BRIEF DESCRIPTION OF THE DRAWINGS

FIG. 5a is a graph showing the stability for each ion species of a conventional-type reference electrode equipped with a polymeric reference electrode membrane comprising a porous polymer and a lipophilic polymer, measured by a potentiometric sensor comprising; a) a conventional-type reference electrode that utilize the reference electrode membrane of the present invention as a working electrode and b) a commercially available salt-bridged orion double junction sleeve-type reference electrode as a reference electrode.

FIG. 5b is a graph showing the sensitivity to hydrogen ion of the same electrode system as in the above FIG. 5a.

FIG. 6b is a graph showing the sensitivity to hydrogen ion of the same electrode system as in the above FIG. 6a.

FIG. 7b is a graph showing the sensitivity to hydrogen ion of the same electrode system as in the above FIG. 7a.

Figure 1:
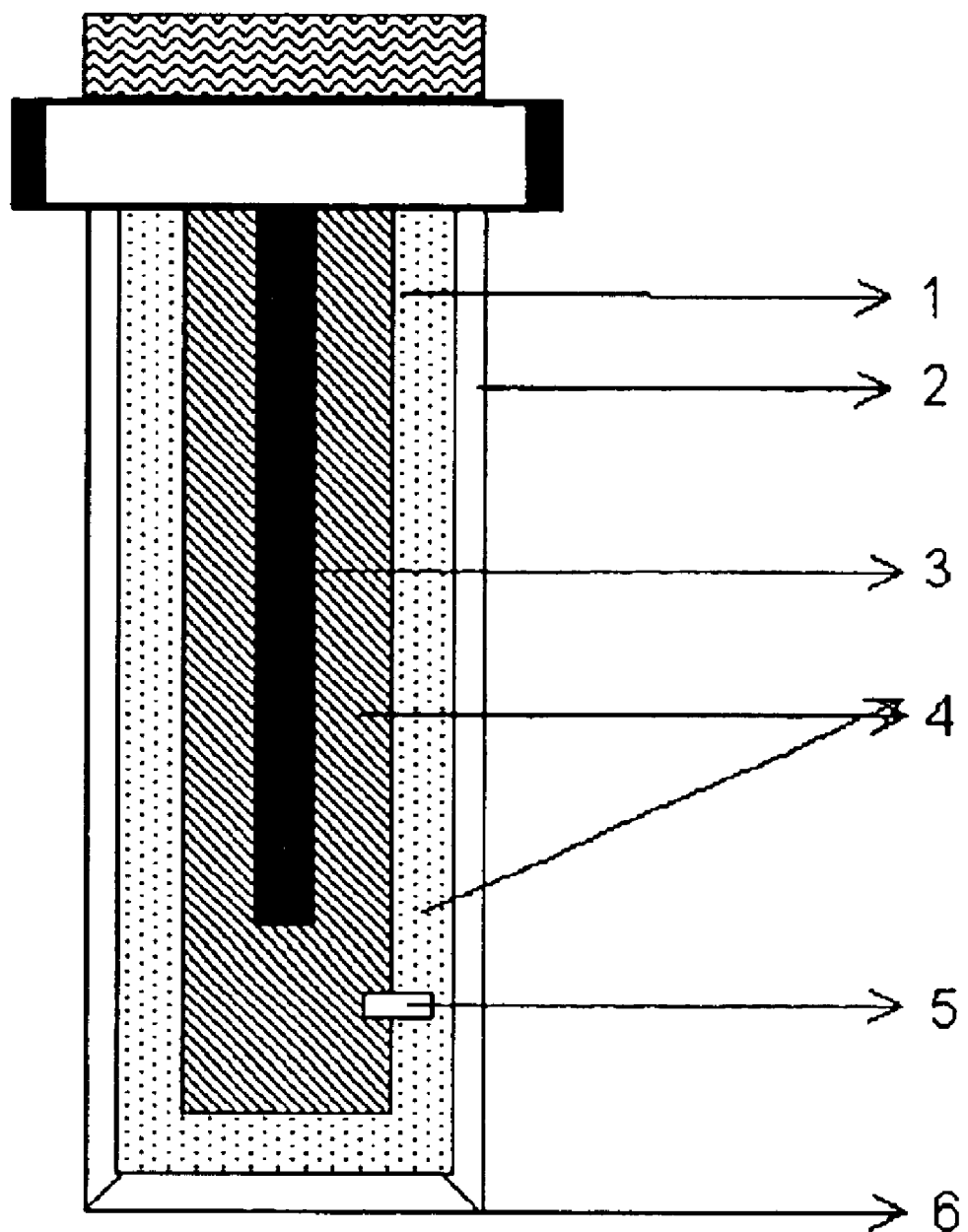
FIG. 1 is a cross sectional view showing a commercially available salt-bridged orion double junction sleeve-type reference electrode.

a) a double layered solid-state reference electrode equipped with a polymeric reference electrode membrane comprising a hydrophilic plasticizer and a lipophilic polymer,
b) a mono-layered reference electrode equipped with a mono-layered polymeric reference electrode membrane comprising a hydrophilic plasticizer and a lipophilic polymer.

1: inner tube
2: outer tube
3: inner reference electrode
4: inner reference solution
5: ceramic frit
6: sleeve
7: inner reference electrolyte
8: polymeric reference electrode membrane
9: insulating film layer
10: substrate
11: reference electrode material
12: hydrogel layer
13: mono-layered polymeric reference electrode membrane
14: sodium ion-selective electrode
15: potassium ion-selective electrode
16: calcium ion-selective electrode
17: chloride ion-selective electrode
18: hydrogen ion-selective electrode

DETAILED DESCRIPTION OF THE INVENTION

The present invention pertains to a polymeric reference electrode membrane comprising (a) one selected from a porous polymer or a hydrophilic plasticizer, (b) a lipophilic polymer, and optionally an adhesion-enhancing material.

The polymeric reference electrode membrane 8 of the present invention is a polymeric reference electrode membrane containing a porous polymer and a lipophilic polymer, or a polymeric reference electrode membrane comprising a hydrophilic plasticizer and a lipophilic polymer. Optionally, the polymeric reference electrode membrane may further comprise an adhesion-enhancing material.

More specifically, the porous polymer introduced to the polymeric reference electrode membrane 8 comprising the porous polymer and the lipophilic polymer is preferably selected from the group consisting of cellulose acetate, cellulose acetate butylate, cellulose triacetate, nitro cellulose and a combination thereof.

The lipophilic polymer plays important role in increasing the adhesion and controlling the porosity by being changed in its addition ratio. The lipophilic polymer is preferably selected from the group consisting of silicone rubber, poly (vinyl chloride), polyurethane, poly (vinyl chloride) carboxylated copolymer or poly (vinyl chloride-co-vinyl acetate-co-vinyl alcohol) and at least one thereof.

The polymeric reference electrode membrane 8 comprises 5–70% by weight of the porous polymer and 30–95% by weight of the lipophilic polymer, and optionally, may further comprise 0.001–1.0% weight of an adhesion-enhancing material based on total weight of the composition. Preferably, the composition comprises 10–50% by weight of the porous polymer and 50–90% by weight of the lipophilic polymer, and more preferably, 30% by weight of the porous polymer and 70% by weight of the lipophilic polymer. If the amount of the porous polymer is less than 5% weight, the membrane is hypersensitive to various ion species in sample solutions and thus it is unfavorable. Meanwhile, if the amount exceeds 70% by weight, the reference electrode membrane is not formed or the lifetime of the electrode is shortened.

The hydrophilic plasticizer introduced to the polymeric reference electrode membrane 8 comprising the hydrophilic plasticizer and the lipophilic polymer is selected from the group consisting of glycerol, polyethylene glycol, ethylene glycol monomethyl ether, ethylene glycol, formamide.

The hydrophilic plasticizer in the polymeric reference electrode membrane 8 plays a role in solidifying the lipophilic polymer and absorbing water from the air to dissolve salts during its storage. Additionally, it allows ions to pass through the membrane, acts as a buffer. Based on these functions, the hydrophilic plasticizer activates the reference electrode and thus can shorten the preconditioning time required for the sample detection of the reference electrode.

Additionally, the lipophilic polymer introduced to the polymeric reference electrode membrane 8 comprising the hydrophilic plasticizer and the lipophilic polymer functions as a separation membrane and prevents electrolyte from rapidly diffusing into sample solutions, thereby extending the electrode to lifetime. The lipophilic polymer is also used same material selected from the polymeric reference electrode membrane 8 comprising the porous polymer and the lipophilic polymer.

In the present invention, the composition comprises the amount of 20–70% by weight of the hydrophilic plasticizer and in the amount of 30–80% by weight of the lipophilic polymer. Optionally, the adhesion-enhancing material is added in the amount of 0.01% by weight based on the membrane composition.

As for the adhesion-enhancing material, its addition aims to ensure sufficient adhesion between the polymeric reference electrode membrane and the reference electrode equipped with the polymeric reference electrode membrane 8. In order to further increase the adhesion, the adhesion-enhancing material is added in the amount of 0.001–1.0% by weight, on a basis of the total composition constituting the polymeric reference electrode membrane. A suitable adhesion-enhancing material is selected from the group of the silicon compounds with high reactivity. Examples are a diluted silicon tetrachloride ($SiCl_4$), aminopropyltriethoxy silane, N-[3-(trimethoxysilyl)propyl]ethylenediamine, N-(2-aminoethyl)-3-aminopropyltrimethoxy silane, 3-methacryloxypropyltrimethoxy silane, N-(2-(vinylbenzylamino)-ethyl)-3-aminopropyltrimethoxy silane, 3-glycidoxypropyltrimethoxy silane, methyltrimethoxy silane and phenyltrimethoxy silane.

The present invention provides a conventional-type reference electrode equipped with the polymeric reference electrode membrane.

Referring to FIG. 1, there is shown a cross section of a commercially available salt-bridged orion double junction sleeve-type reference electrode. The double junction consisting of an inner tube 1 and an outer tube 2 surrounds the electrode body, which is fixed to an inner reference electrode 3 and which is filling with an inner reference solution 4. Additionally, a ceramic frit 5 and a sleeve 6 are fixed to an end of the electrode.

Figure 2:
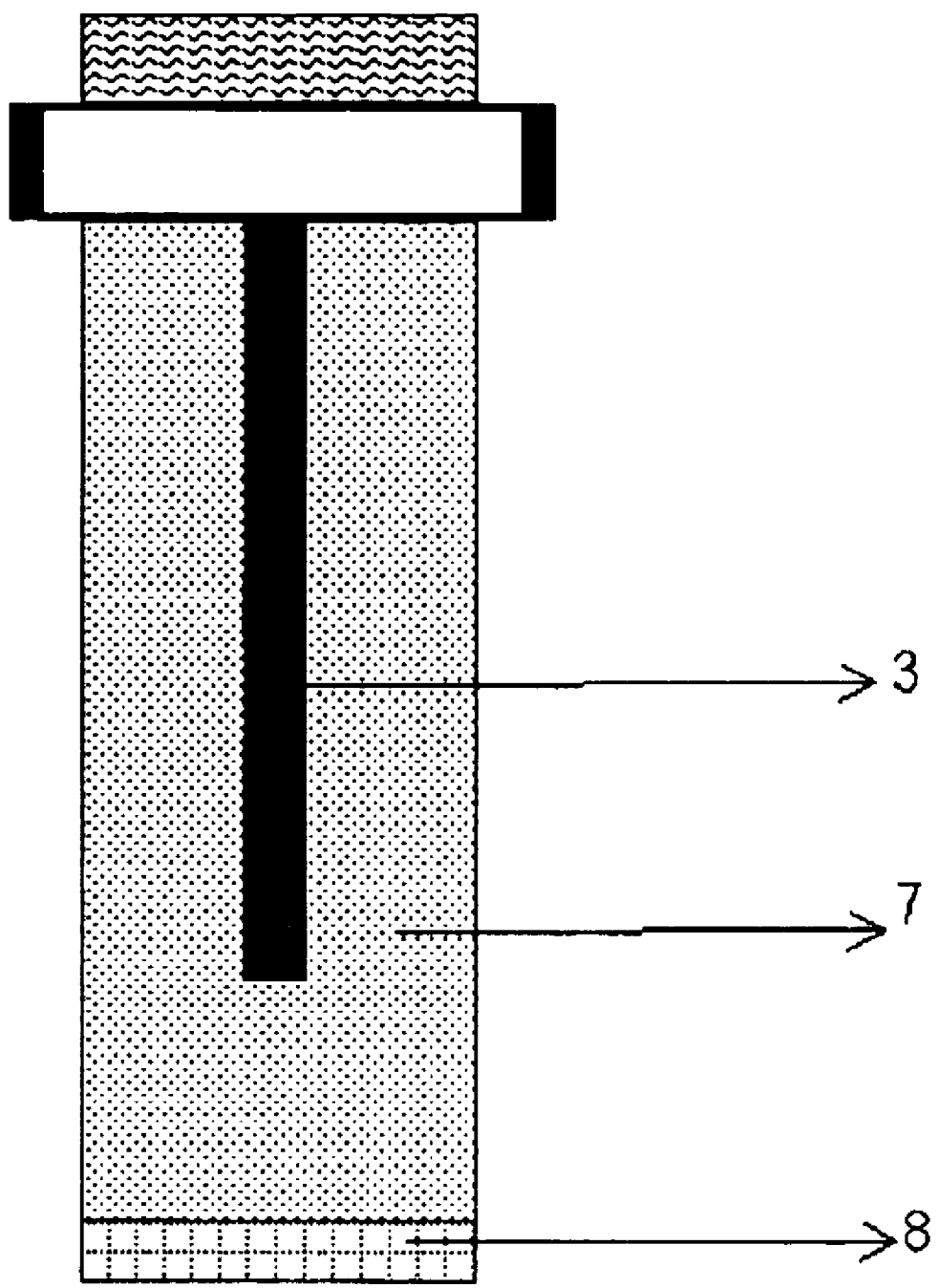
FIG. 2 is a cross sectional view showing a conventional-type reference electrode equipped with the polymeric reference electrode membrane of the present invention.

In FIG. 2 is shown a conventional-type reference electrode equipped with the polymeric reference electrode membrane 8 of the present invention, which comprises an inner reference electrode 3 positioned at the center within the electrode body; an inner reference electrolyte 7 filling the internal space of the electrode body; and a polymeric reference electrode membrane 8 mounted to an end of the electrode.

The inner reference electrolyte 7 in a conventional-type reference electrode, which fills the space within the conventional-type reference electrode, is prepared by dissolving a salt, having similar mobility in distilled water. Said the salt is selected from the group consisting of KCl, NaCl, $KNO_3$ and $NH_4NO_3$. Occasionally, the inner reference electrolyte 7 may be replaced with a hydrogel and thus be extended the electrode lifetime by slow releasing the electrolytes. As for, the hydrogel is used by dissolving a hydrophilic polymer at an amount of 1–15% by weight in 0.01–3.0 M salt-saturated aqueous solution, in which the salt is selected from the group consisting of KCl, NaCl, $KNO_3$ and $NH_4NO_3$, having similar mobility.

The hydrophilic polymer is preferably selected from the group consisting of polyvinylpyrrolidone, polyvinyl alcohol, poly (methyl methacrylate), agar, gelatin and at least one thereof.

The inner reference electrolyte 7 in the conventional-type reference electrode connects smoothly different phases.

As the above polymeric reference electrode membrane 8, both of the polymeric reference electrode membranes 8 prepared from a porous polymer and a lipophilic polymer, and from a hydrophilic plasticizer and a lipophilic polymer, can be used.

More specifically, in the conventional-type reference electrode equipped with the polymeric reference electrode membrane 8 comprising the porous polymer and the lipophilic polymer, the preconditioning time required for sample detection can be shortened owing to the porosity of the porous polymer itself. As well, the porosity makes the inner reference electrolyte 7 slowly flow out to maintain constant potential. Hence, the reference electrode is more stable for each ion and for a long period of time.

The present invention provides a double layered or a mono-layered solid-state reference electrode equipped with the polymeric reference electrode membrane of the present invention.

Figure 3A:
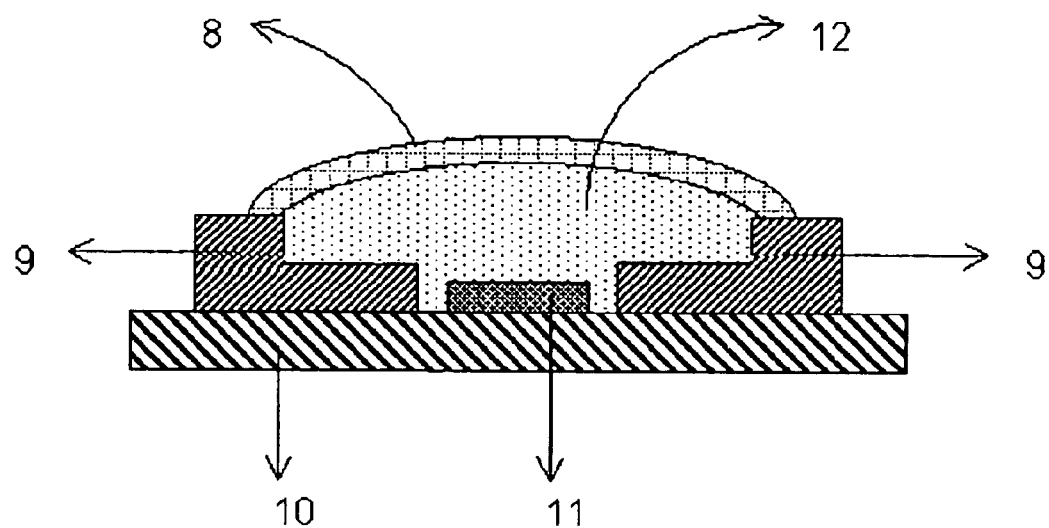
FIG. 3a is an illustrative example showing a double layered solid-state reference electrode equipped with the polymeric reference electrode membrane of the present invention.

As can be seen in FIG. 3a, a double layered solid-state reference electrode equipped with the polymeric reference electrode membrane of the present invention comprises; a) a substrate 10; b) an insulating film layer 9 formed on the substrate 10; c) a reference electrode material 11 insulated by the insulating film layer 9 in aqueous solutions; d) a hydrogel layer 12 covered with the reference electrode material 11; and e) a polymeric reference electrode membrane 8 additionally fixed to the hydrogel layer 12.

As the above polymeric reference electrode membrane 8, both of the polymeric reference electrode membranes prepared from a porous polymer and a lipophilic polymer, and from a hydrophilic plasticizer and a lipophilic polymer, can be used.

The hydrogel layer 12 is responsible for the same function as the inner reference electrolyte 7 in the conventional-type reference electrode extending the lifetime of the electrode in sample solutions. In particular, in the case of the polymeric reference electrode membrane 8 containing the porous polymer and the lipophilic polymer, the hydrogel layer 12 is rapidly hydrated because of the porosity of the porous polymer itself, and thus the preconditioning time of the electrode is shortened, therefore, being reduced a total measuring time.

In the double layered solid-state reference electrode of present invention, the polymeric reference electrode membrane 8 is formed on the hydrogel layer 12.

The double layered solid-state reference electrode of present invention can overcome poor adhesion for the conventional one by improving the adhesion of the porous polymeric reference electrode membrane itself and by adding the additional adhesion-enhancing material. Thus, the reference electrode of the present invention has improved reproducibility and yield.

Figure 3B:
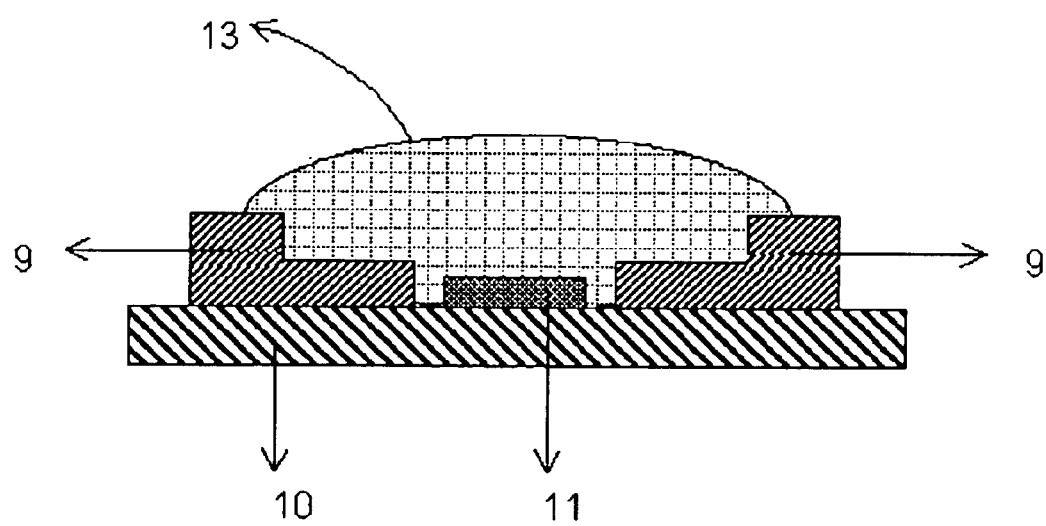
FIG. 3b is an illustrative example showing a mono-layered solid-state reference electrode equipped with a mono-layered polymeric reference electrode membrane of the present invention.

As can be seen in FIG. 3b, the mono-layered solid-state reference electrode containing the mono-layered polymeric reference electrode membrane 13 comprises; a) a substrate 10; an insulating film layer 9 formed on the substrate 10; a reference electrode material 11 insulated by the insulating film layer 9 in aqueous solutions; and a mono-layered polymeric reference electrode membrane 13 for protecting the reference electrode material 11.

The mono-layered polymeric reference electrode membrane 13 is prepared by dissolving a composition comprising 20–70% by weight of a hydrophilic plasticizer saturated with a salt selected from the group consisting of KCl, NaCl, $KNO_3$ and $NH_4NO_3$ and 30–80% by weight of a lipophilic polymer in an organic solvent, adding an adhesion-enhancing material at an amount of 0.01% by weight to the composition. Preferably, the organic solvent should have a large dielectric constant for dissolving the hydrophilic plasticizer and the lipophilic polymer and be exemplified by dimethylformamide, nitromethane and acetonitrile.

In the mono-layered solid-state reference electrode, the hydrophilic plasticizer plays a role in the reference electrode by slowly releasing the electrolyte and constantly maintaining a liquid-liquid contact potential. Wherein, the hydrophilic plasticizer is saturated with a salt selected from the group consisting of KCl, NaCl, $KNO_3$ and $NH_4NO_3$.

The substrate 10 is preferably made of a material selected from the group consisting of alumina-containing ceramics, silicon, poly (vinyl chloride), polyester, polycarbonate, and semiconductor materials.

As described above, the insulating film layer 9 is provided for separating the electrode material from the sample solution. Preferably, a dielectric film, which is inexpensive, easy to form, and superior in insulating properties in aqueous solutions, is used for the insulating film layer 9.

The reference electrode material 11 is selected from ionic conductive material such as silver/silver chloride, a metal layer and an insoluble metal salt layer using a screen printing method, a physical or chemical vapor deposition method or etching method.

The hydrogel layer 12 is prepared by dissolving a hydrophilic polymer at an amount of 1–15% by weight in 0.01–3.0 M aqueous solution saturated with a salt selected from the group consisting of KCl, NaCl, $KNO_3$ and $NH_4NO_3$, each of which is similar in mobility.

Examples of the hydrophilic polymer include, but not by way of limitation, polyvinylpyrrolidone, poly (vinyl alcohol), poly (methyl methacrylate), agar or gelatin.

Accordingly, the double layered solid-state reference electrode equipped with a polymeric reference electrode membrane of the present invention is readily miniaturized by using not the inner reference electrolyte but the hydrogel layer, thereby easily developing a miniaturized multiple-potentiometric sensor. Additionally, the mass production of the solid-state reference electrode can be achieved, resulting in reduced production cost. As well, the sensing portions of the electrodes are so small as to require small amounts of samples for analysis.

Further, the present invention provides a multi-potentiometric sensor consisting of a reference electrode selected from a double layered or a mono-layered solid-state reference electrode equipped with the polymeric reference electrode membrane, and a working electrode of a set of ion-selective electrodes.

Figure 4:
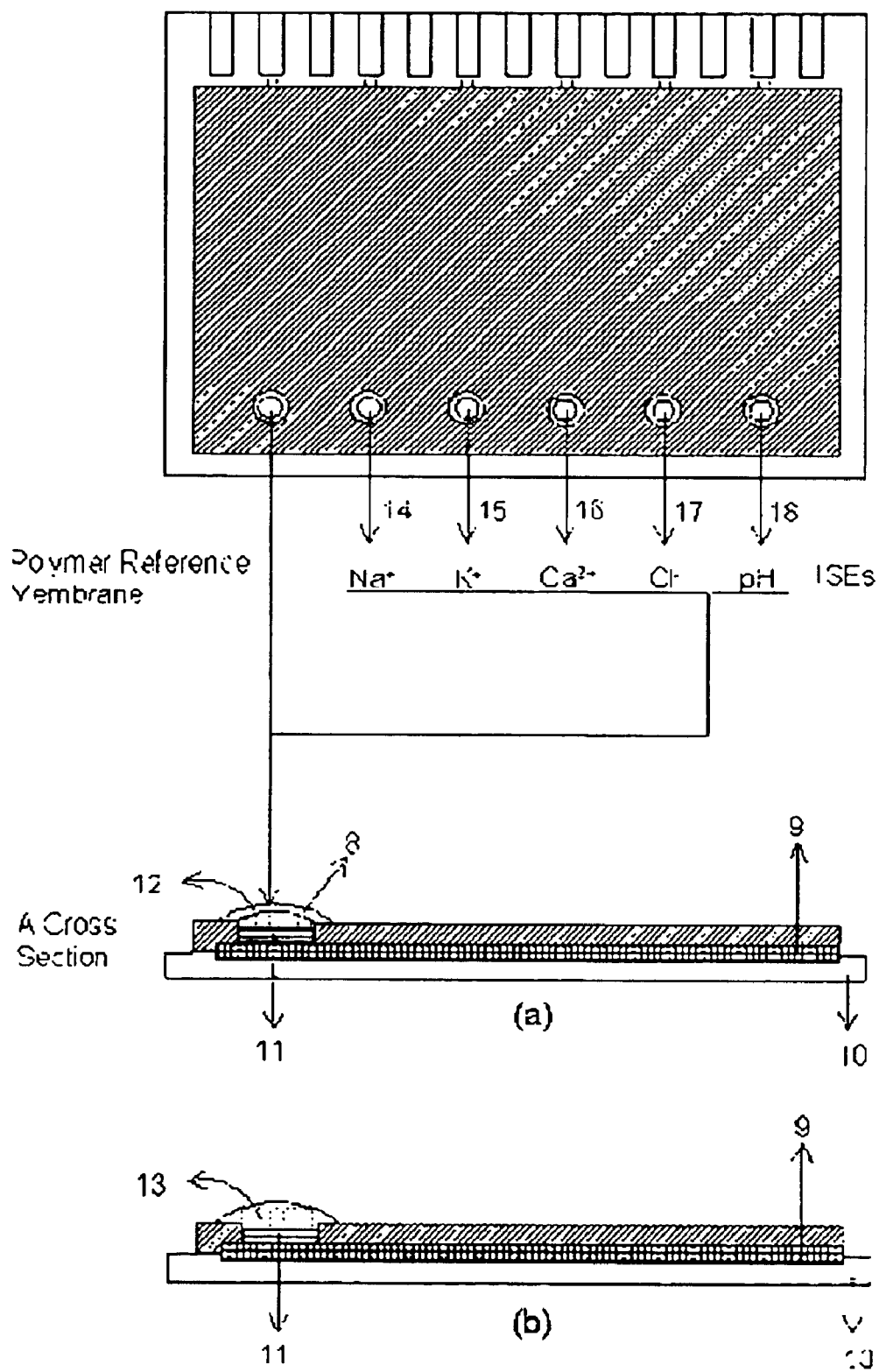
FIG. 4 shows a multi-potentiometric sensor consisting of a reference electrode selected from a double layered or a mono-layered solid-state reference electrode equipped with a polymeric reference electrode membrane of the present invention, and a set of ion-selective electrodes as a working electrode, in which designates a) a potentiometric sensor mounted with the double layered solid-state reference electrode equipped with the polymeric reference electrode membrane and b) a potentiometric sensor mounted with the mono-layered solid-state reference electrode equipped with the mono-layered polymeric reference membrane.

FIG. 4 shows a multi-potentiometric sensor comprising a reference electrode selected from a double layered or a mono-layered solid-state reference electrode equipped with the polymeric reference electrode membrane and at least one of ion-selective electrodes as a working electrode in which reference numeral 14 designates a sodium ion-selective electrode; 15, a potassium ion-selective electrode; 16, a calcium ion-selective electrode; 17, a chloride ion-selective electrode; and 18, a hydrogen ion-selective electrode. In (a) of this figure, the double layered solid-state reference electrode equipped with the polymeric reference electrode membrane is mounted, and in (b), the mono-layered solid-state reference electrode equipped with the mono-layered polymeric reference electrode membrane 13 comprising the hydrophilic plasticizer and the lipophilic polymer is mounted.

More specifically, on one side of the polymeric substrate, a reference electrode selected from the double layered or the mono-layered solid-state reference electrode equipped with the polymeric reference electrode membrane is fixed. Then, at least one ion-selective electrodes as a working electrode is arranged in a row at a distance from the reference electrode on a single chip, thereby fabricating the potentiometric sensor, capable of being used as a multiple-ion sensor.

A better understanding of the present invention may be obtained in light of the following examples which are set forth to illustrate, but are not to be construed to limit the present invention.

1. Preparation of Polymeric Reference Electrode Membrane

EXAMPLE 1

Preparation of Polymeric Reference Electrode Membrane Comprising the Porous Polymer and the Lipophilic Polymer Based on the composition having the highest yield, 30% by weight of celluolose acetate and 70% by weight of polyurethane were dissolved in THF, poured into a glass ring having a diameter of 22 mm and then dried for one day, to prepare a polymeric reference electrode membrane 8.

EXAMPLE 2

Preparation of Polymeric Reference Electrode Membrane Comprising the Hydrophilic Plasticizer and the Lipophilic Polymer 38% by weight of glycerol and 27% by weight of formamide were added to 35% by weight of polyurethane in THF. As an adhesion-enhancing material, N-[3-trimethoxysilyl]

propyl]ethylenediamine was added at an amount of 0.001 mg per 100 mg of the composition to obtain a polymeric reference electrode membrane 8 comprising the hydrophilic plasticizer and the lipophilic polymer.

EXAMPLE 3

Preparation of Mono-Layered Polymeric Reference Electrode Membrane Comprising the Hydrophilic Plasticizer and the Lipophilic Polymer 30% by weight of glycerol saturated with KCl as an electrolyte and 30% by weight of formamide were added to 40% by weight of polyurethane in THF to give a composition. As an adhesion-enhancing material, N-[3-trimethoxysilyl)propyl]ethylenediamine was added at an amount of 0.001 mg per 100 mg of the composition to obtain a mono-layered polymeric reference electrode membrane 13.

2. Preparation of Conventional-Type Reference Electrode

EXAMPLE 4

Preparation of Conventional-type Reference Electrode Equipped with the Polymeric Reference Electrode Membrane Comprising the Porous Polymer and the Lipophilic Polymer 2 M KCl aqueous solution as an inner reference electrolyte 7 was filled in a space of electrode body containing inner reference electrode 3. The polymeric reference electrode membrane 8 comprising the porous polymer and the lipophilic polymer prepared as in the above example 1 was cut to a diameter of 5.5 mm, and then mounted to a Philips electrode body, to manufacture a conventional-type reference electrode equipped with the polymeric reference electrode membrane 8 comprising the porous polymer and the lipophilic polymer (FIG. 2).

EXAMPLE 5

Preparation of Conventional-Type Reference Electrode Equipped with Polymeric Reference Electrode Membrane Comprising the Hydrophilic Plasticizer and the Lipophilic Polymer 2 M KCl aqueous solution as an inner reference electrolyte 7 was filled in a space of electrode body containing inner reference electrode 3. The polymeric reference electrode membrane 8 comprising the hydrophilic plasticizer and the lipophilic polymer prepared in example 2 was cut to a diameter of 5.5 mm, and then mounted to Philips electrode body, to prepare a conventional-type reference electrode equipped with the polymeric reference electrode membrane 8 comprising the hydrophilic plasticizer and the lipophilic polymer (FIG. 2).

3. Preparation of Solid-State Reference Electrode

EXAMPLE 6

Preparation of Double Layered Solid-State Reference Electrode Equipped with the Polymeric Reference Electrode Membrane Comprising the Porous Polymer and the Lipophilic Polymer A hydrogel layer 12, serving as the inner reference electrolyte 7 in a conventional-type reference electrode, was preparated by dissolving 6% by weight of polyvinylpyrrolidone in 3 M KCl aqueous solution. As an adhesion-enhancing material, N-[3-(trimethoxysillyl)propyl] ethylenediamine was added at an amount of 0.001–1.0 wt % based on the total weight of the composition for polymeric reference electrode membrane 8 comprising the porous polymer and the lipophilic polymer, to fabricate a porous polymeric reference electrode membrane.

Electrode materials of a working electrode and a reference electrode are formed deposing silver paste on an alumina substrate 10 through a screen-printing method. An insulating film layer 9 was also screen-printed between the working electrode metal layer and the reference electrode metal layer. Thereafter, the alumina substrate 10, on which the reference electrode material 11 formed as a metal layer and the insulating film layer 9 are fixed, was immersed in 1 M $FeCl_3$ solution for about 2 minutes, thereby forming insoluble silver chloride salt layer on the metal layer. The hydrogel layer 12 covered with the electrode system fabricated on alumina substrate 10. And then the composition of the polymeric reference electrode membrane 8 comprising a porous polymer and a lipophilic polymer was poured on the hydrogel layer 12 and dried at room temperature for 24 hours, to fabricate a double layered solid-state reference electrode comprising the porous polymeric reference electrode membrane (FIG. 3a).

EXAMPLE 7

Preparation of Double Layered Solid-State Reference Electrode Equipped with the Polymeric Reference Electrode Membrane Comprising the Hydrophilic Plasticizer and the Lipophilic Polymer A double layered solid-state reference electrode equipped with polymeric reference electrode membrane 8 comprising a hydrophilic plasticizer and a lipophilic polymer was fabricated in the same manner as in the above example 6, except that the polymeric reference electrode membrane 8 comprising the hydrophilic plasticizer and the lipophilic polymer prepared as in the above example 2 was used (FIG. 3a).

EXAMPLE 8

Preparation of Mono-layered Solid-State Reference Electrode Equipped with the Mono-Layered Polymeric Reference Electrode Membrane Comprising the Hydrophilic Plasticizer and the Lipophilic Polymer A mono-layered solid-state reference electrode equipped with mono-layered polymeric reference electrode membrane 13 was fabricated in the same manner as in the above example 6, except that the mono-layered polymeric reference electrode membrane 13 comprising the hydrophilic plasticizer and the lipophilic polymer prepared as in the above example 3 was used (FIG. 3b).

4. Preparation of Potentiometric Sensor

EXAMPLE 9

Fabrication of Potentiometric Sensor Provided with Double Layered Solid-State Reference Electrode Equipped with the Polymeric Reference Electrode Membrane Comprising the Porous Polymer and the Lipophilic Polymer The Double layered solid-state reference electrode equipped with the polymeric reference electrode membrane 8 comprising the porous polymer and the lipophilic polymer was mounted to one side of the polymeric substrate. Then, at least one ion-selective electrodes selected from $Na^+$, $K^+$, $Ca^{2+}$, $Cl^-$ and $H^+$ was arranged in a row with the reference electrode on a single chip, to fabricate a potentiometric sensor, capable of being detected a multiple ion (FIG. 4).

Hereinafter, measurements conducted to determine the characteristics of the conventional-type reference electrode and the solid-state reference electrode equipped with polymeric reference electrode membrane of the present invention are described.

EXPERIMENTAL EXAMPLE 1

Stability for Each Ion Species and Lifetime of the Conventional-Type Reference Electrode Equipped with the Polymeric Reference Electrode Membrane Comprising the Porous Polymer and the Lipophilic Polymer In order to determine the electrode lifetime through stability for each ion species and stability of long period of time for the conventional-type reference electrode equipped with polymeric reference electrode membrane 8 comprising the porous polymer and the lipophilic polymer prepared as in the above example 4, the following experiments were performed.

The potential difference between the working electrode and the reference electrode was measured in a Tris (tris (hydroxymethyl)aminomethane) buffer, pH 7.4, by use of a potentiometer equipped with a high-impedance input 16-channel A/D converter.

An electrode system was composed of a commercially available salt-bridged orion double junction sleeve-type reference electrode as a reference electrode, and a conventional-type reference electrode equipped with the porous polymeric reference electrode membrane prepared as in the above example 4 as a working electrode.

As seen in FIG. 5a, the conventional-type difference electrode equipped with the porous polymeric reference electrode membrane comprising the porous polymer and the lipophilic polymer shows the stability for 300 mM sodium ion ($Na^+$), 100 mM potassium ion ($K^+$), 100 mM calcium ion ($Ca^{2+}$), 100 mM salicylate ion ($Sal^-$), and 300 mM chloride ion ($Cl^-$).

Additionally, in order to investigate the sensitivity to pH in same electrode system as in the above FIG. 5a, 11.4 mM boric acid, 6.7 mM citric acid and 10 mM $NaH_2PO_4$ were prepared as blank electrolytes and NaOH was used as a sample solution. From the experimental results of FIG. 5b, it can be seen that the conventional-type reference electrode shows the stability for hydrogen ions ($H^+$) over a broad pH range of 3–12.

Figure 5C:
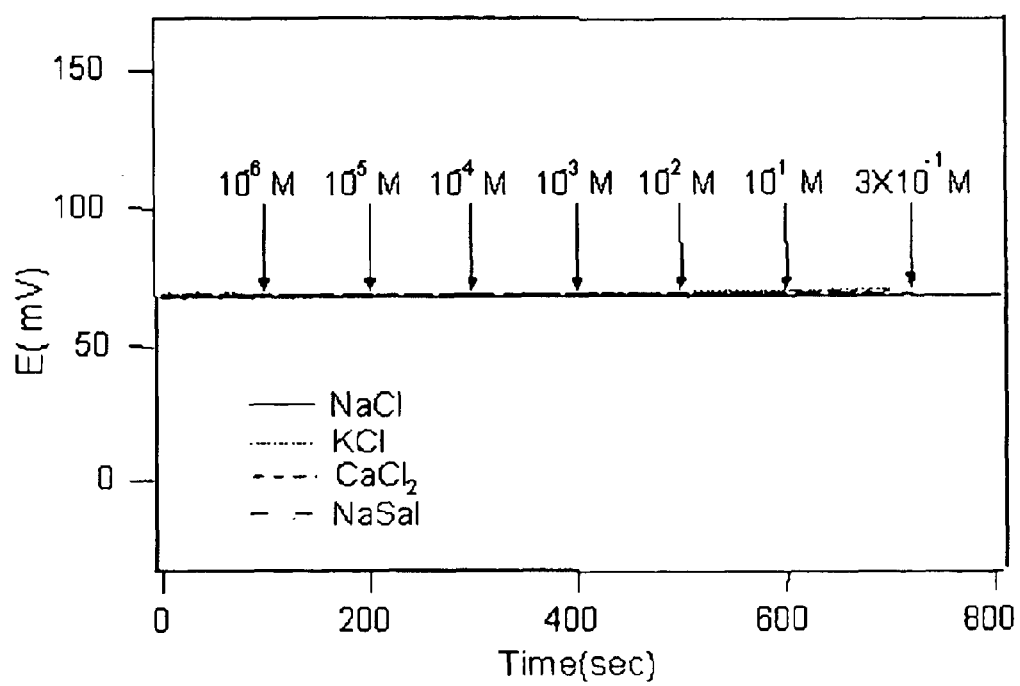
FIG. 5c is a graph showing the stability of long period of time for each ion of the same electrode system as in the above FIG. 5a, after 157 days.

FIG. 5c shows the stability of long period of time for each ion species using the same electrode system as in the above FIG. 5a. As seen the result, even after being stored at room temperature in aqueous solutions for as long as 157 days, the conventional-type reference electrode observed same stability for each ion species.

Figure 5D:
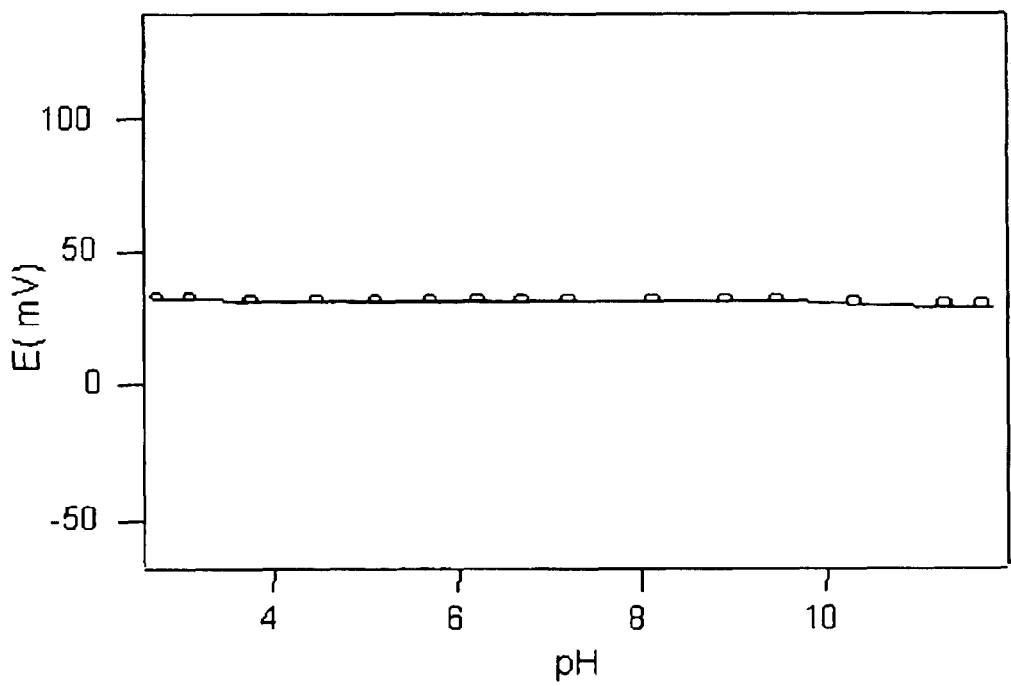
FIG. 5d is a graph showing the stability for hydrogen ion of the same electrode system as in the above FIG. 5a, after 157 days.

Likewise, as shown in FIG. 5d, the conventional-type reference electrode prepared as in the above example 4 has stability for hydrogen ions ($H^+$) over a broad pH range of 3–12, even after being stored at room temperature in aqueous solutions for as long as 157 days.

EXPERIMENTAL EXAMPLE 2

Stability for Each Ion Species and Lifetime of Conventional-Type Reference Electrode Equipped with the Polymeric Reference Electrode Membrane Comprising the Hydrophilic Plasticizer and the Lipophilic Polymer To determine the electrode lifetime through stability for each ion species and for a long period time of the conventional-type reference electrode equipped with polymeric reference electrode membrane 8 comprising the hydrophilic plasticizer and the lipophilic polymer prepared as in the above example 5, the following experiments were carried out.

A potentiometric sensor having the same structure as in the above experimental example 1 was performed except using a conventional-type reference electrode equipped with the polymeric reference electrode membrane comprising the hydrophilic plasticizer and the lipophilic as a working electrode.

Figure 6A:
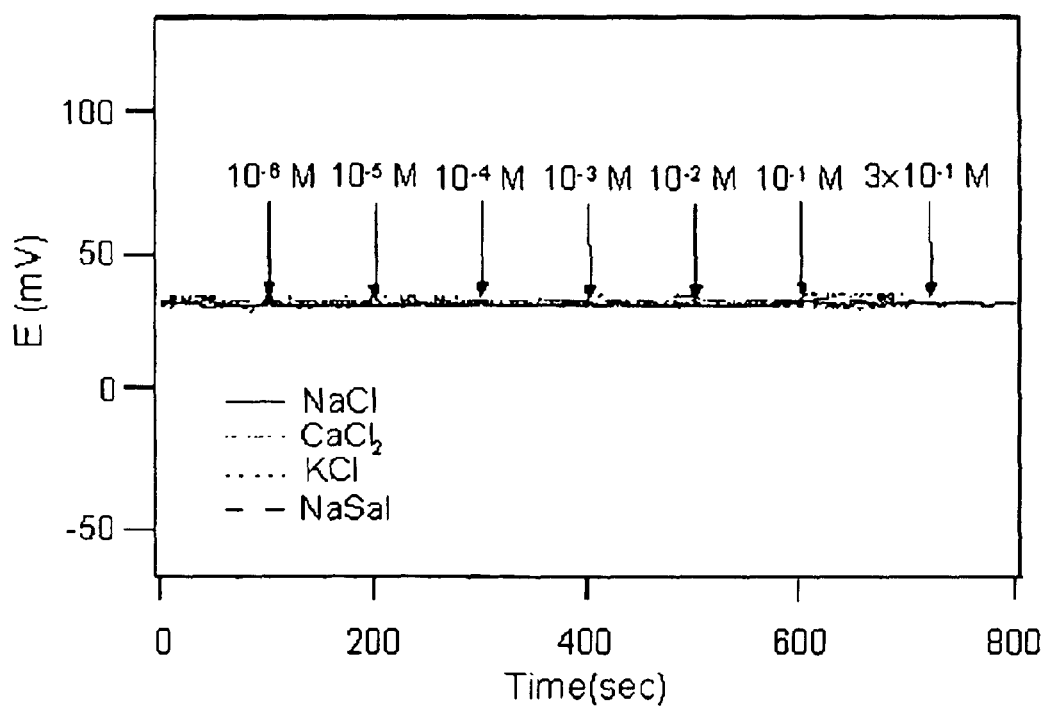
FIG. 6a is a graph showing the stability for each ion of a conventional-type reference electrode equipped with a polymeric reference electrode membrane comprising a hydrophilic plasticizer and a lipophilic polymer, measured by potentiometric sensor comprising; a) a working electrode of a conventional-type reference electrode of the present invention and b) a reference electrode of a commercially available salt-bridged orion double junction sleeve-type reference electrode.

As can be seen in FIG. 6a, the conventional-type reference electrode equipped with the polymeric reference electrode membrane 8 comprising the hydrophilic plasticizer and the lipophilic polymer shows stability for each ion species from aqueous solutions of 100 mM sodium ion ($Na^+$), 300 mM sodium ion ($Na^+$), 10 mM potassium ion ($K^+$), 10 mM calcium ion ($Ca^{2+}$) and 10 mM salicylate ion ($Sal^-$).

Figure 6B:
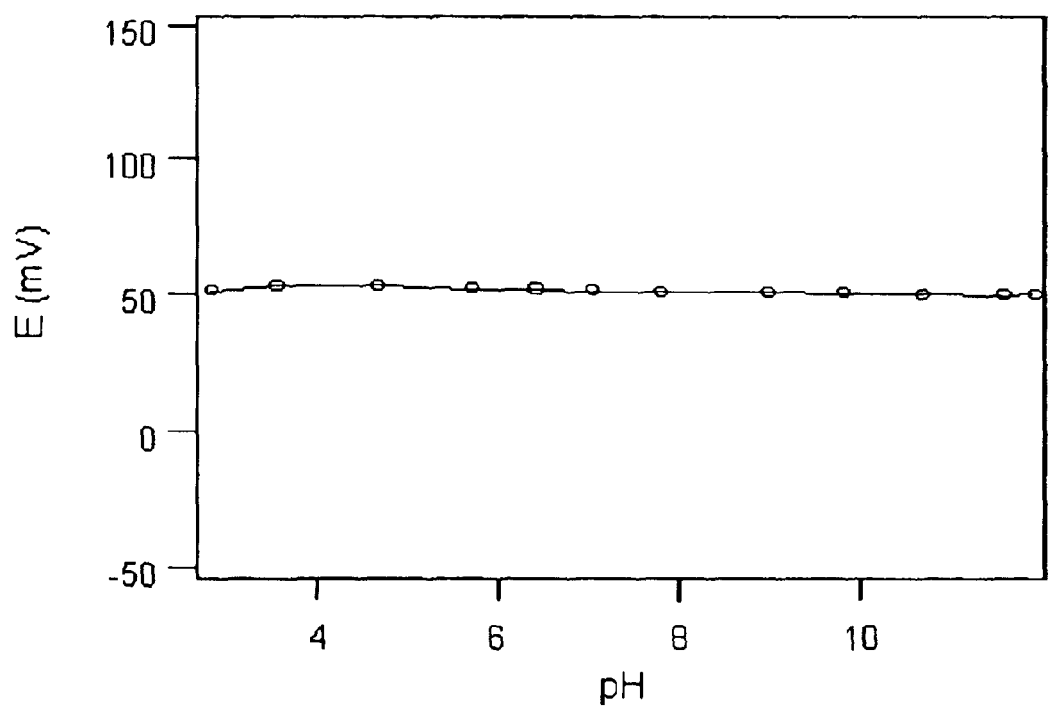

In order to investigate the stability to pH, 11.4 mM boric acid, 6.7 mM citric acid and 10 mM $NaH_2PO_4$ were prepared as blank electrolytes and NaOH was used as a sample solution. From the experimental results of FIG. 6b, it can be seen that the conventional-type reference electrode equipped with the polymeric reference electrode membrane 8 comprising the hydrophilic plasticizer and the lipophilic polymer shows stability for hydrogen ions ($H^+$) over a broad pH range of 3–12.

Figure 6C:
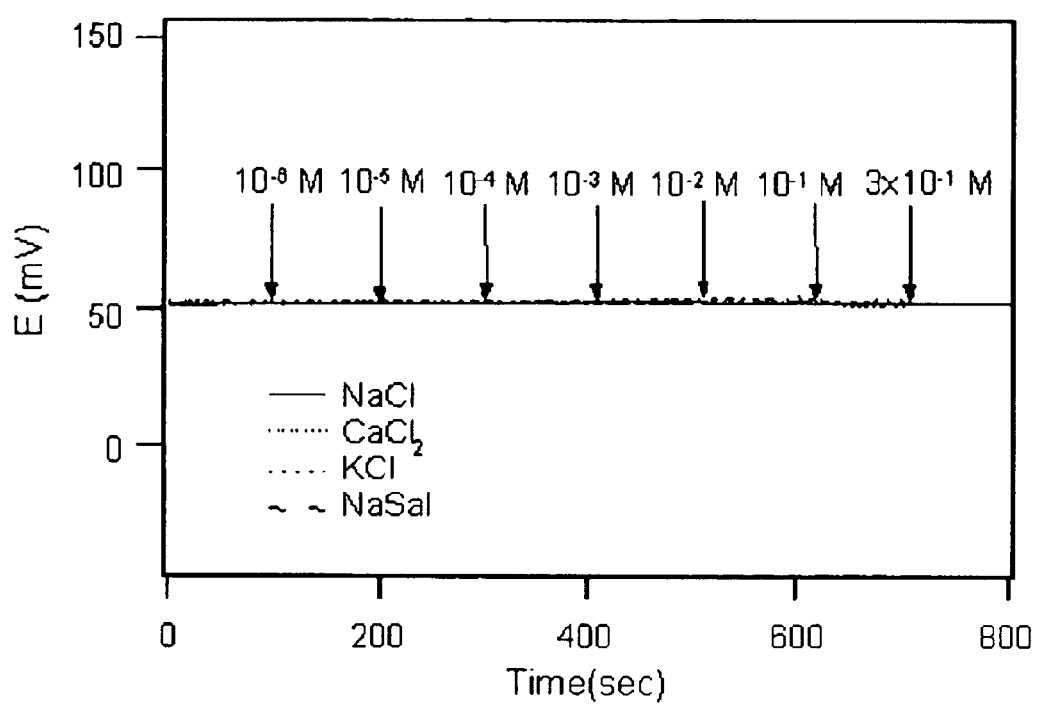
FIG. 6c is a graph showing stability of the long period of time for each ion species of the same electrode system as in the above FIG. 6a, after 95 days.

As can be seen in FIG. 6c, the conventional-type reference electrode equipped with the polymeric reference electrode membrane 8 comprising the hydrophilic plasticizer and the lipophilic polymer has the same stability of long period of time for each ion species, even after being stored in blood for as long as 95 days.

Figure 6D:
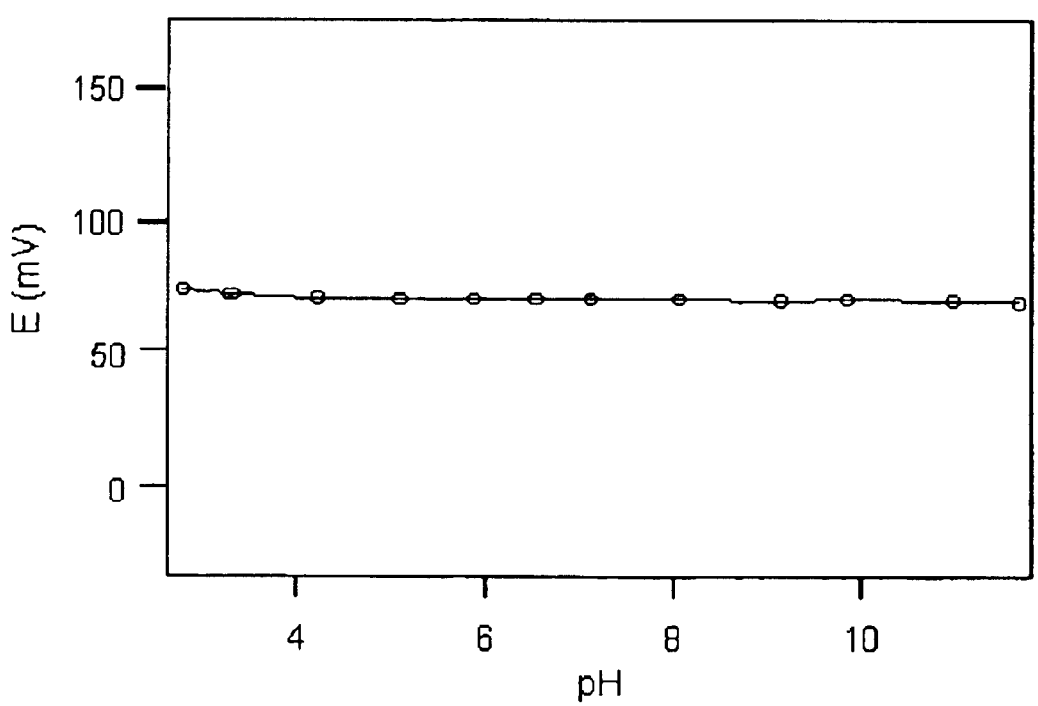
FIG. 6d is a graph showing the stability for hydrogen ion of the same electrode system as in the above FIG. 6a, after 95 days.

Likewise, as shown in FIG. 6d, the conventional-type reference electrode as above has stability for hydrogen ions ($H^+$) over a broad pH range of 3–12, even after being stored in bloods for as long as 95 days.

EXPERIMENTAL EXAMPLE 3

Stability for Each Ion of Double Layered Solid-state Reference Electrode Equipped with Polymeric Reference Electrode Membrane Comprising the Porous Polymer and the Lipophilic Polymer To determine the stability for each ion species of a double layered solid-state reference electrode equipped with the polymeric reference electrode membrane 8 comprising the porous polymer and the lipophilic polymer prepared as in the above example 6, the following experiments were conducted.

This experiment was carried out in the same manner as in the above experimental example 1, except that, in the electrode system, the double layered solid-state reference fabricated as in the above example 6 served as a working electrode.

Figure 7A:
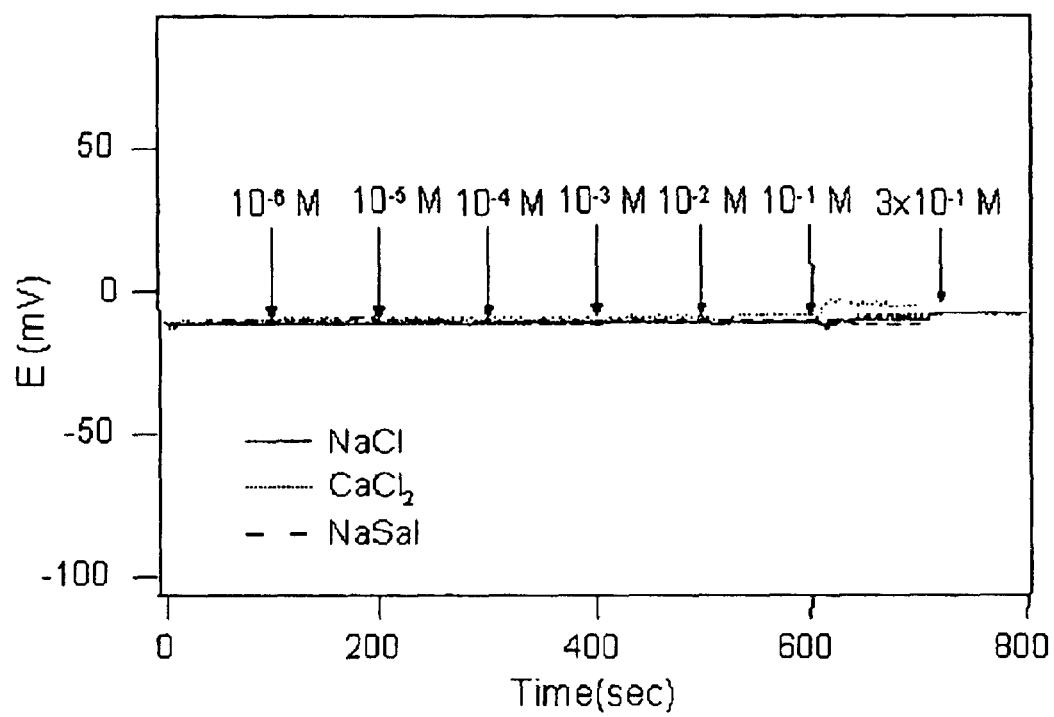
FIG. 7a is a graph showing the stability for each ion of a double layered solid-state reference electrode equipped with a polymeric reference electrode membrane comprising a porous polymer and a lipophilic polymer, measured by potentiometric sensor comprising; a) a double layered solid-state reference electrode of the present invention as a working electrode and b) a commercially available salt-bridged orion double junction sleeve-type reference electrode as a reference electrode.

As can be seen in FIG. 7a, the double layered solid-state reference electrode prepared as in the above example 6, shows the stability for 300 mM sodium ion ($Na^+$), 100 mM calcium ion ($Ca^{2+}$) and 100 mM salicylate ion ($Sal^-$).

Figure 7B:
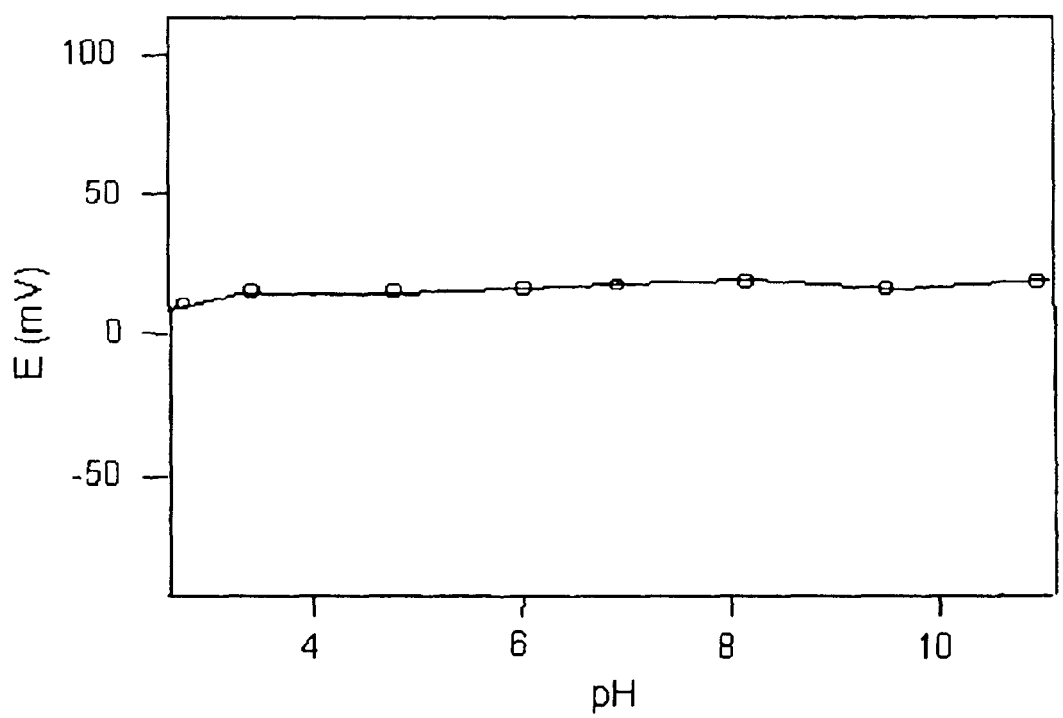

In order to investigate the stability to pH, 11.4 mM boric acid, 6.7 mM citric acid and 10 mM $NaH_2PO_4$ were prepared as blank electrolytes and NaOH was used as sample solution. From the experimental results of FIG. 7b, it can be seen that the double layered solid-state reference fabricated as in the above example 6 shows stability for hydrogen ions (H⁺) over a broad pH range of 3–12.

EXPERIMENTAL EXAMPLE 4

Stability for Each Ion Species of Double Layered Solid-State Reference Electrode Equipped with Polymeric Reference Electrode Membrane Comprising the Hydrophilic Plasticizer and the Lipophilic Polymer In order to determine the stability for each ion species of the double layered solid-state reference electrode equipped with the polymeric reference electrode membrane 8 comprising the hydrophilic plasticizer and the lipophilic polymer prepared as in the above example 7, the following experiments were performed.

The potential difference between the working electrode and the reference electrode was measured in the same manner as in the above experimental example 1, except using the double layered solid-state reference electrode prepared as in the above example 7.

Figure 8:
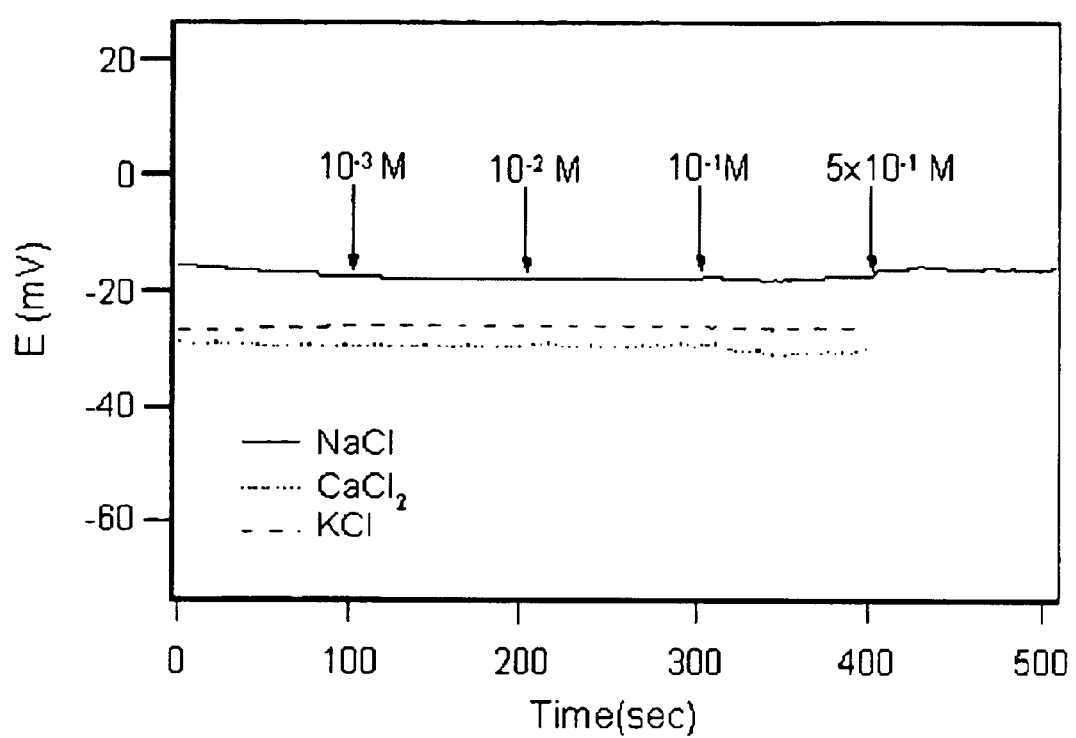
FIG. 8 is a graph showing the stability for each ion of a double layered solid-state reference electrode equipped with a polymeric reference electrode membrane comprising a hydrophilic plasticizer and a lipophilic polymer, measured by potentiometric sensor comprising; a) a working electrode of a double layered solid-state reference electrode of the present invention and b) a reference electrode using a commercially available salt-bridged orion double junction sleeve-type reference electrode.

From the results of FIG. 8, it can be seen that the double layered solid-state reference electrode prepared as in the above example 7 shows stability for 100 mM potassium ion (K⁺), 500 mM sodium ion (Na⁺) and 100 mM calcium ion (Ca²⁺)

EXPERIMENTAL EXAMPLE 5

Stability for Each Ion Species of Mono-Layered Solid-State Reference Electrode Equipped with the Polymeric Reference Electrode Membrane Comprising the Hydrophilic Plasticizer and the Lipophilic Polymer The mono-layered solid-state reference electrode equipped with polymeric reference electrode membrane 8 comprising the hydrophilic plasticizer and the lipophilic polymer prepared as in the above example 8, was measured for its stability to various ion species as follows.

The potential difference between the working electrode and the reference electrode was measured in the same manner as in the above experimental example 1, except that, in the electrode system, the mono-layered solid-state reference electrode prepared as in the above example 8 as a working electrode.

Figure 9A:
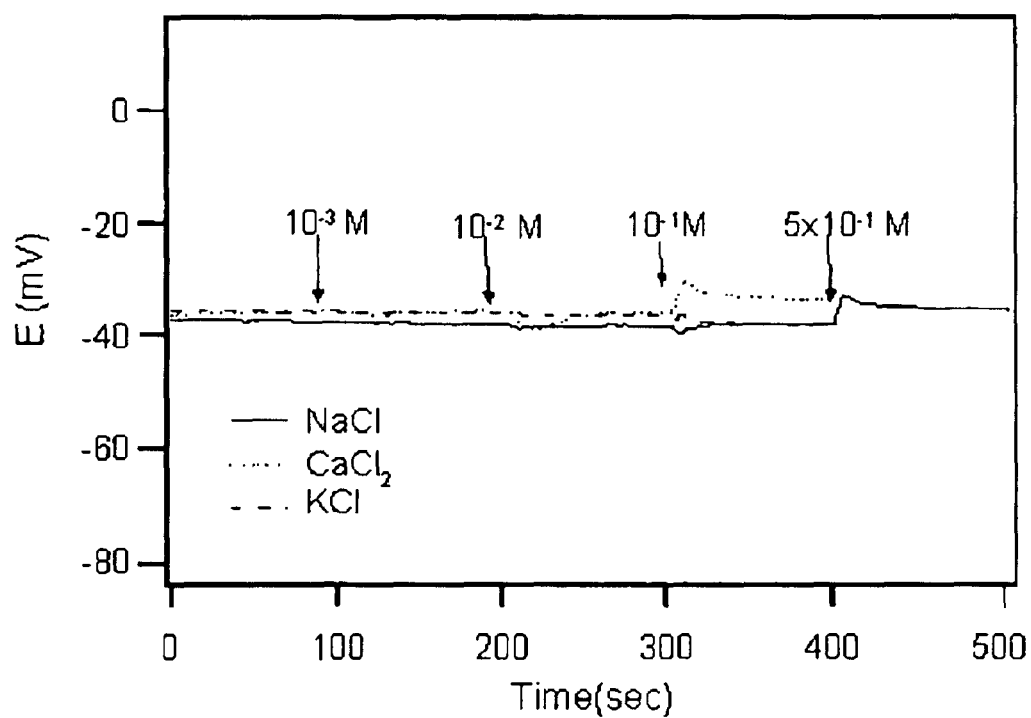
FIG. 9a is a graph showing the stability for each ion of a mono-layered solid-state reference electrode equipped with a polymeric reference electrode membrane comprising a hydrophilic plasticizer and a lipophilic polymer, measured by potentiometric sensor comprising; a) a working electrode of a mono-layered solid-state reference electrode of the present invention and b) a reference electrode using a commercially available salt-bridged orion double junction sleeve-type reference electrode.

As can be seen in FIG. 9a, the mono-layered solid-state reference electrode equipped with polymeric reference electrode membrane 8 comprising the hydrophilic plasticizer and the lipophilic polymer shows stability for 100 mM potassium ion (K⁺), 500 mM sodium ion (Na⁺) and 100 mM calcium ion (Ca²⁺).

Figure 9B:
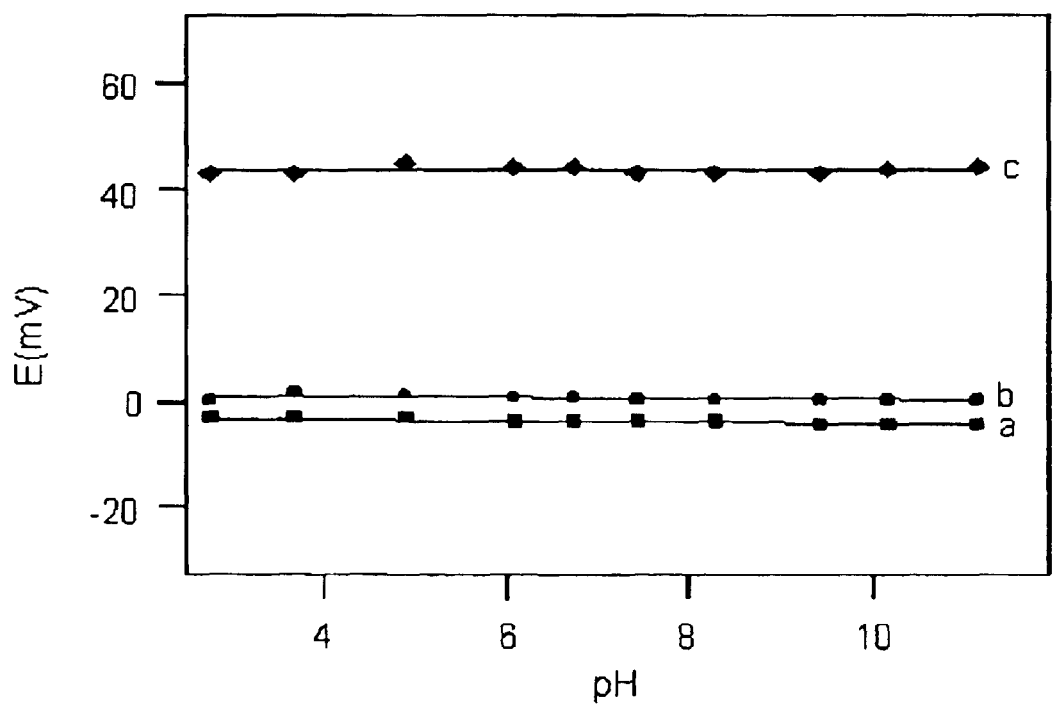
FIG. 9b is a graph showing the stability for hydrogen ion of a solid-state reference electrode equipped with a polymeric reference electrode membrane comprising a hydrophilic plasticizer and a lipophilic polymer, wherein, a) a double layered solid-state reference electrode;
b) a mono-layered solid-state reference electrode; and
c) a commercially available salt-bridged orion double junction sleeve-type reference electrode.

In FIG. 9b, in order to investigate the stability to pH of the solid-state reference electrode equipped with polymeric reference electrode membrane comprising the hydrophilic plasticizer and the lipophilic polymer, 11.4 mM boric acid, 6.7 mM citric acid and 10 mM $NaH_2PO_4$ were used as blank electrolytes and NaOH was used as sample solution In this figure, (a) shows a double layered solid-state reference electrode; (b), a mono-layered polymeric reference electrode; and (c), a commercially available salt-bridged orion double junction sleeve-type reference electrode 1. These electrodes show the stability for hydrogen ions (H⁺) over a broad pH range of 3–12.

Figure 10:
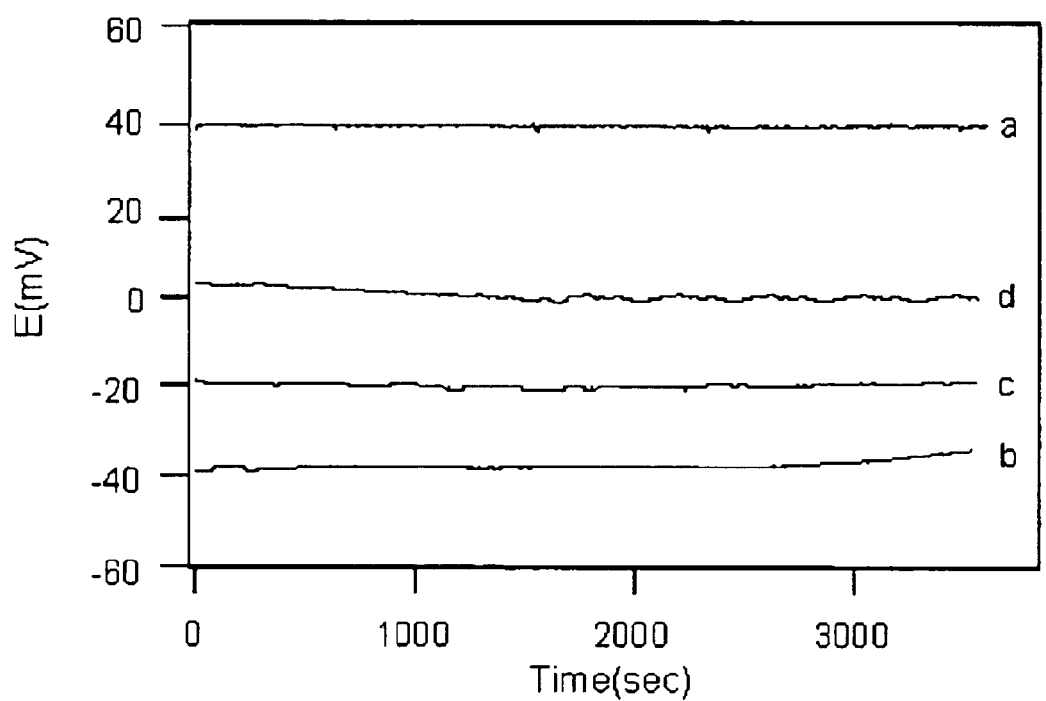
FIG. 10 is a graph showing the stability for time of a solid-state reference electrode equipped with a polymeric reference electrode membrane of the present invention, wherein, a) a double layered solid-state reference electrode equipped with the polymeric reference electrode membrane comprising a porous polymer and a lipophilic polymer;
b) a double layered solid-state reference equipped with a polymeric reference electrode membrane comprising a hydrophilic plasticizer and a lipophilic polymer;
c) a mono-layered solid-state reference electrode equipped with a mono-layered polymeric reference electrode membrane comprising a hydrophilic plasticizer and lipophilic polymer; and
d) a commercially available salt-bridged orion double junction sleeve-type reference electrode.

From the result of FIG. 10, it can be seen that the solid-state reference electrodes equipped with polymeric reference electrode membrane 8 fabricated as in the above examples 6, 7 and 8 have the stability of the time.

In this drawing, (a) shows a double layered solid-state reference electrode equipped with polymeric reference electrode membrane 8 comprising a porous polymer and lipophilic polymer; (b), a double layered solid-state reference electrode equipped with polymeric reference electrode membrane 8 comprising a hydrophilic plasticizer and lipophilic polymer; (c), a mono-layered solid-state reference electrode equipped with a mono-layered polymeric reference electrode membrane 13 comprising a hydrophilic plasticizer and lipophilic polymer; and (d), a commercially available salt-bridged orion double junction sleeve type reference electrode. As apparent from FIG. 10, All solid-state reference electrodes provided with a polymeric reference electrode membrane of the present invention were found to maintain constant potential for 1 hour. Particularly, in a double layered solid-state reference electrode equipped with a porous polymeric reference electrode membrane comprising a porous polymer and a lipophilic polymer, the precondition time is stabilized within 100 seconds, and thus the double layered solid-state reference electrode is favorably usable at the point-of care.

EXPERIMENTAL EXAMPLE 6

Performance Comparison of Solid-State Potentiometric Sensor Containing a Double Layered Solid-state Reference Electrode Equipped with the Polymeric Reference Electrode Membrane Comprising the Porous Polymer and the Lipophilic Polymer To fabricate a potentiometric sensor, the electrode system comprises a reference electrode and a working electrode selected from the group consisting of Na⁺, K⁺, Ca²⁺Cl⁻ and H⁺ ion-selective electrodes. As the reference electrode, the double layered solid-state reference electrode equipped with the polymeric reference electrode membrane prepared as in the above example 6, or a commercially available salt-bridged orion double junction sleeve-type reference was then measured for its performance.

Figure 11A:
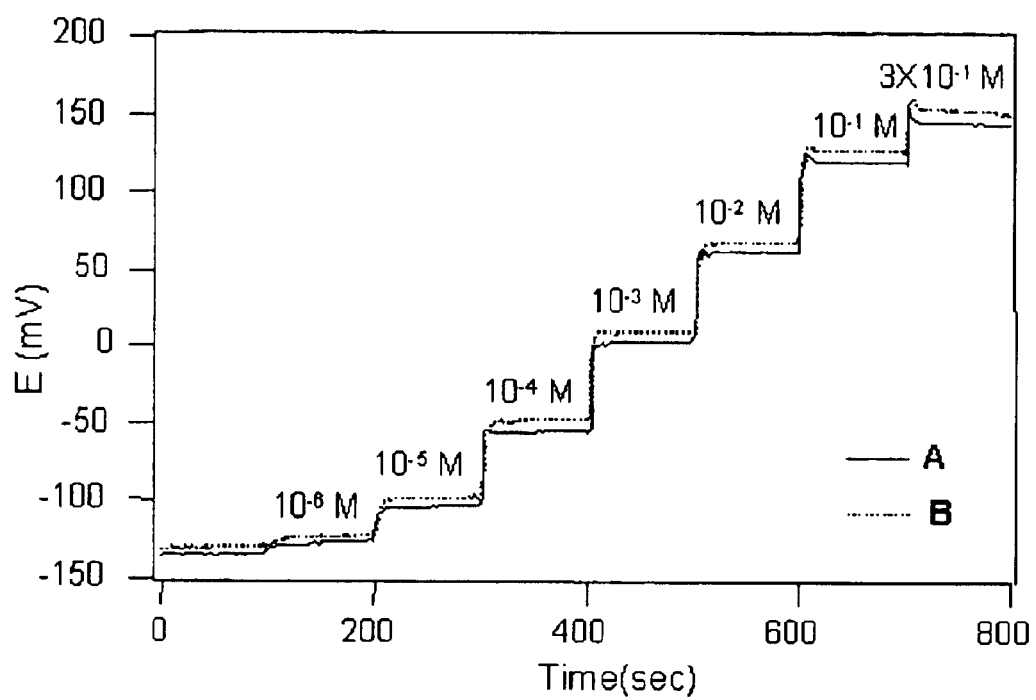
FIG. 11a is a graph showing the potential vs. the time of sodium ions in a sodium ion-selective electrode, measured by potentiometric sensor comprising; a) a working electrode of an ion-selective electrode and b) a reference electrode selected from a double layered solid-state reference electrode equipped with a polymeric reference electrode membrane comprising a porous polymer and a lipophilic polymer, or a commercially available salt-bridged orion double junction sleeve-type reference electrode.
Figure 11B:
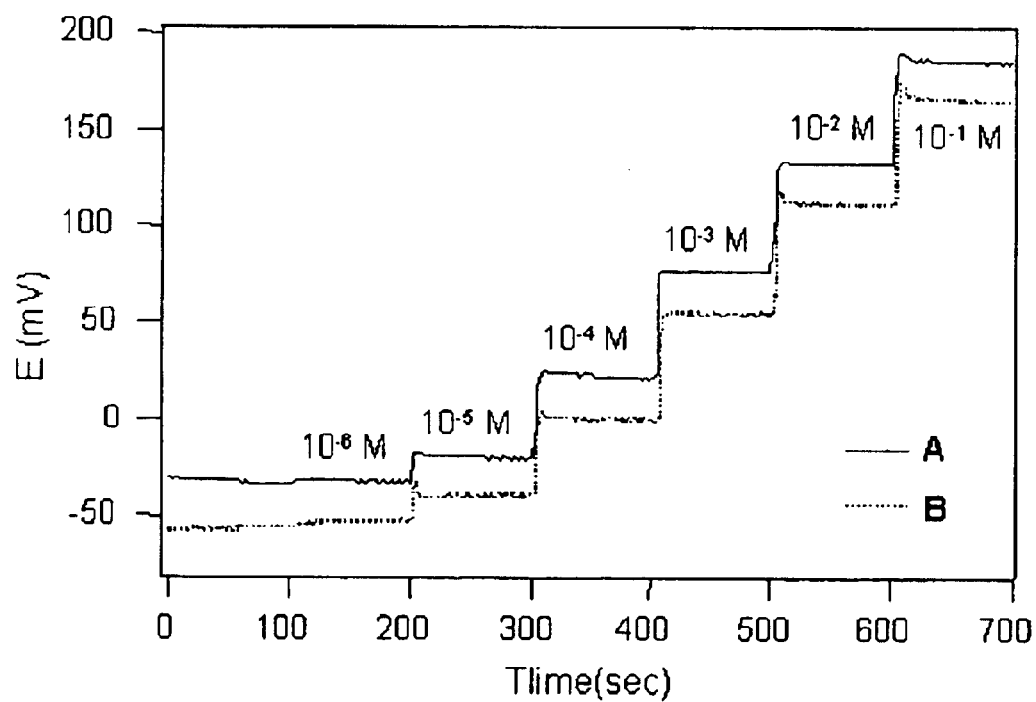
FIG. 11b is a graph showing the potential vs. the time of potassium ions in a potassium ion-selective electrode, serving as a working electrode.
Figure 11C:
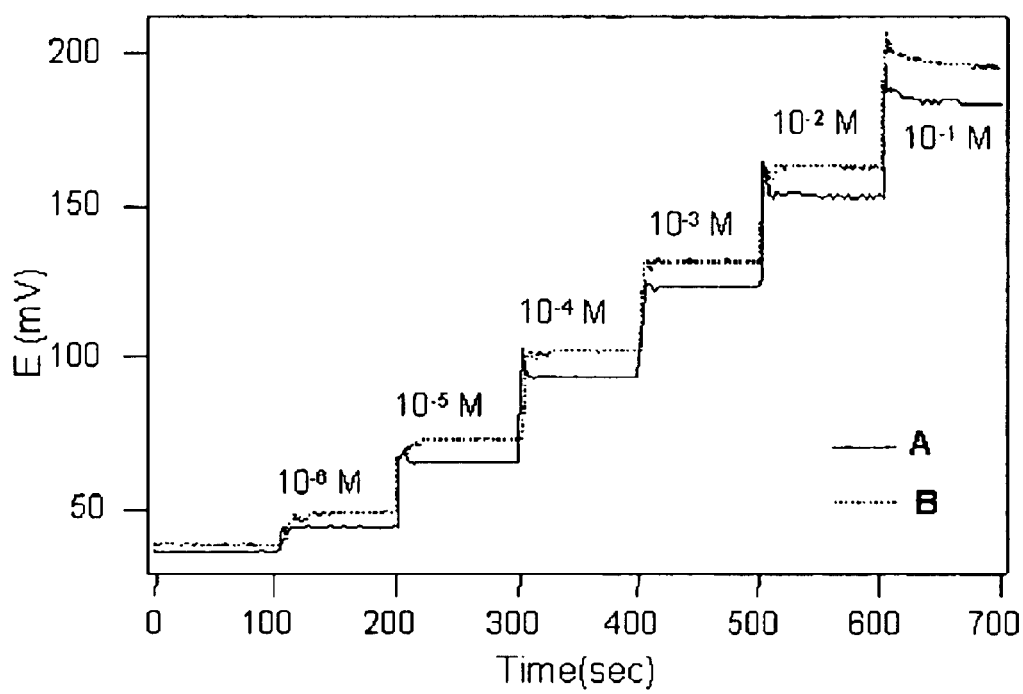
FIG. 11c is a graph showing the potential vs. the time of calcium ions in a calcium ion-selective electrode, serving as a working electrode.
Figure 11D:
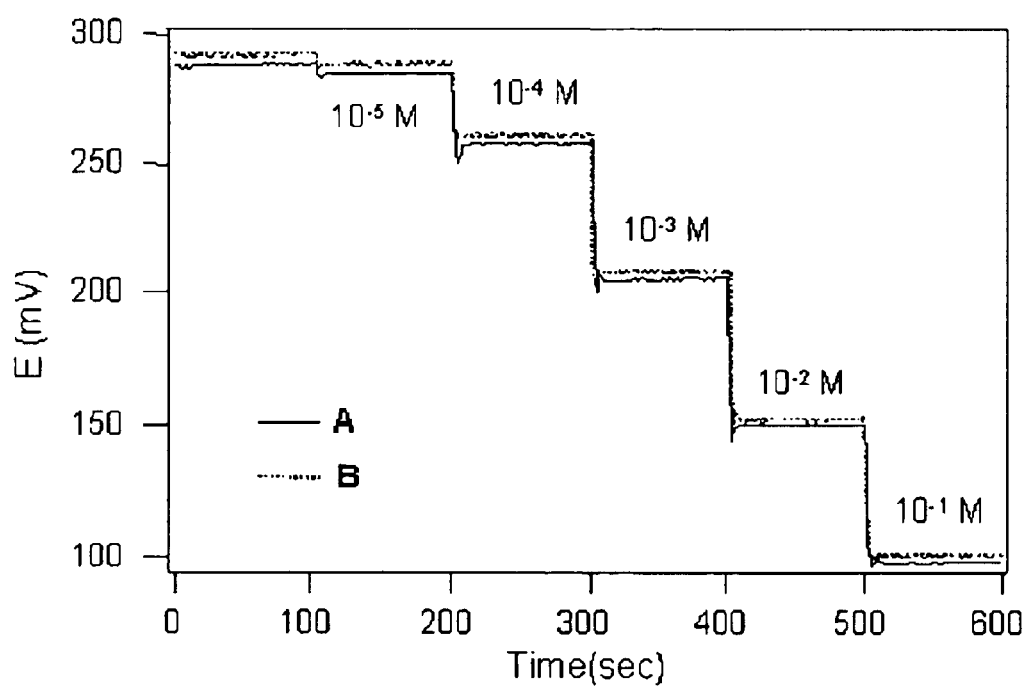
FIG. 11d is a graph showing the potential vs. the time of chloride ions in a chloride ion-selective electrode, serving as a working electrode.
Figure 11E:
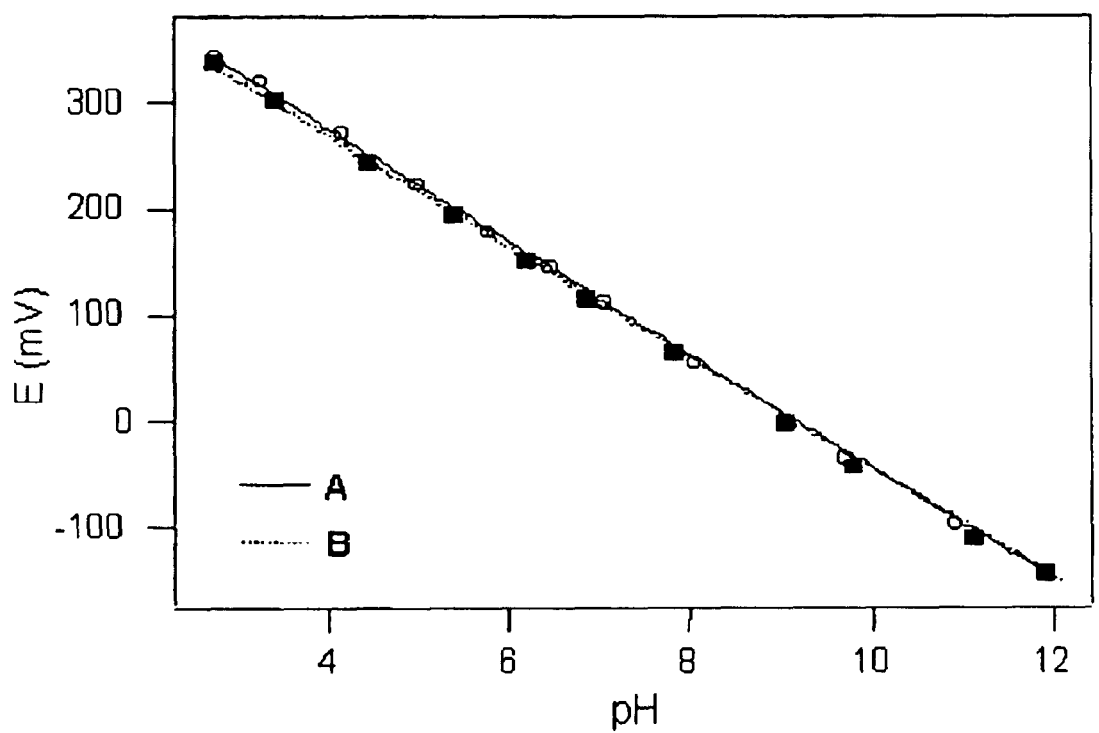
FIG. 11e is a graph showing the potential vs. the time of hydrogen ions in a hydrogen ion-selective electrode, serving as a working electrode, in which each line represents A: the double layered solid-state reference electrode equipped with a polymeric reference electrode membrane comprising a porous polymer and a lipophilic polymer, and
B: the commercially available salt-bridged orion double junction sleeve-type reference electrode.

FIG. 11a is a diagram showing the dynamic sensitivity of a sodium ion-selective electrode as a working electrode; FIG. 11b, a potassium ion-selective electrode; FIG. 11c, a calcium ion-selective electrode; FIG. 11d, a chloride ion-selective electrode; and FIG. 11e, a hydrogen ion-selective electrode.

In these figures, the data from of the potentiometric sensor equipped with the double layered solid-state reference electrode prepared as in the above example 6 is shown as (A), and the data from the potentiometric sensor equipped with a commercially available salt-bridged orion double junction sleeve-type reference electrode 1 is shown as (B).

As can be seen in FIGS. 11a to 11e, the results measured for each ion species of the working electrodes accorded with the data from a double layered solid-state reference electrode prepared as in the above example 6 and from a commercially available salt-bridged orion double junction sleeve-type reference electrode, as a reference electrode. Such high reproducibility makes the reference electrodes of the present invention reliable. Thus, the reference electrodes of the present invention can be introduced to the potentiometric sensor as a miniaturized multiple-ion sensor.

EXPERIMENTAL EXAMPLE 7

Determination Ion Concentration of Unknown Sample using Double Layered Solid-State Reference Electrode Equipped with the Polymeric Reference Electrode Membrane Comprising the Porous Polymer and the Lipophilic Polymer To determine the ion concentration of unknown sample and its precision, this experiment was carried out in the electrode system comprising at least one selected from a potassium or a hydrogen ion electrode as a working electrode and a double layered solid-state reference electrode prepared as in the above example 6 as a reference electrode.

Figure 12A:
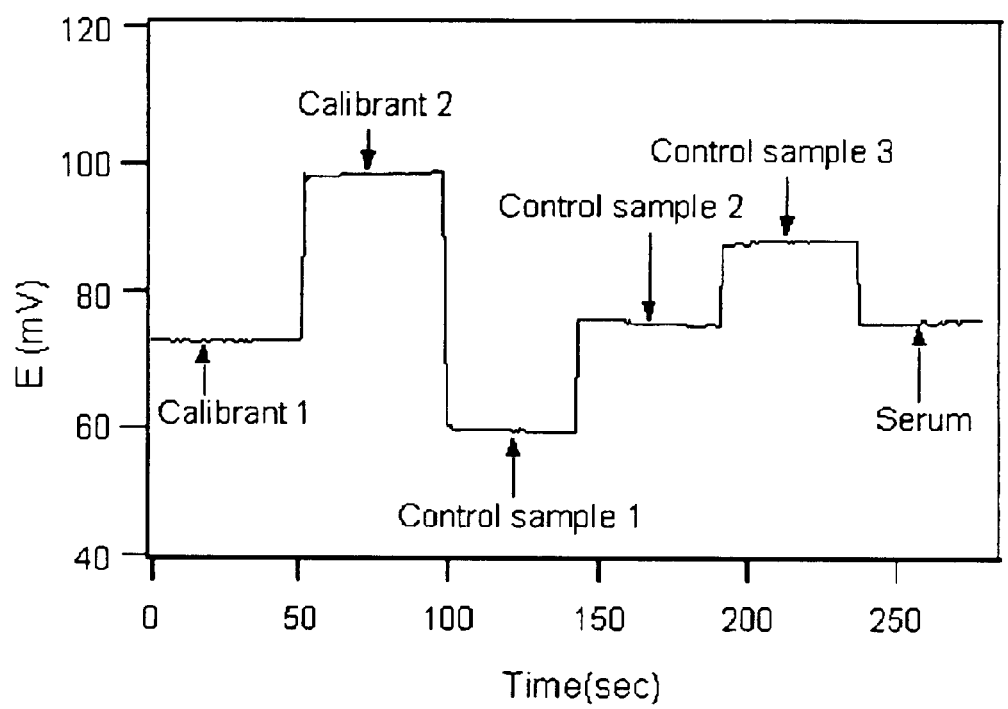
FIG. 12a is a diagram showing the dynamic sensitivity for potassium ion in unknown samples, measured by potentiometric sensor comprising; a) a working electrode of a potassium ion-selective electrode, and b) a reference electrode of a double layered solid-state reference electrode equipped with a polymeric reference electrode membrane comprising a porous polymer and a lipophilic polymer.
Figure 12B:
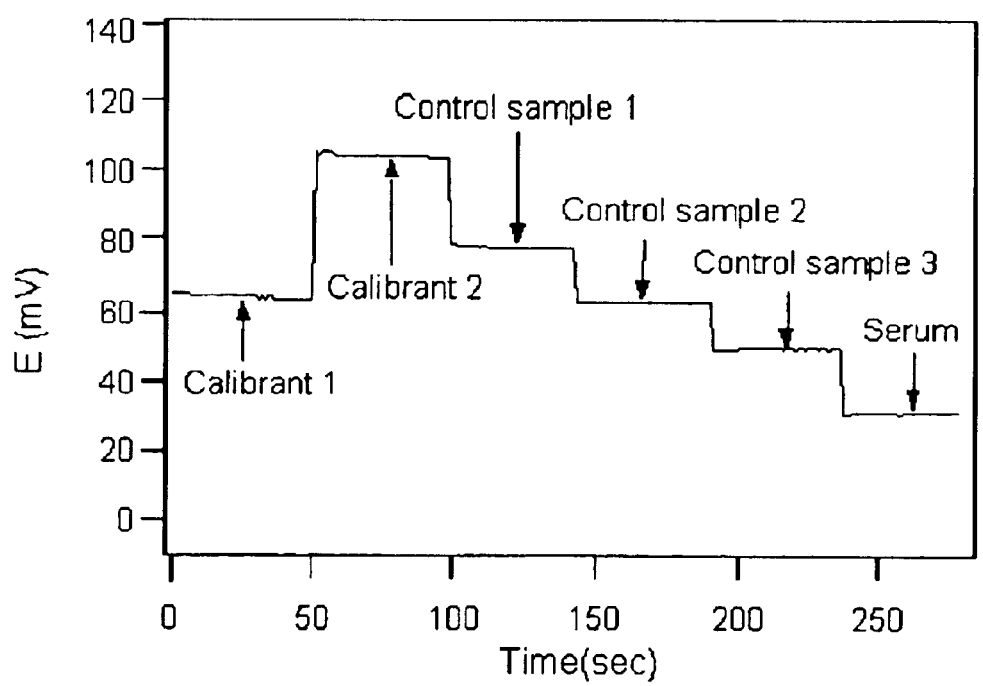
FIG. 12b is a diagram showing the dynamic sensitivity for potassium ion in unknown samples, measured by potentiometric sensor comprising the same reference electrode as in the above FIG. 12a and a hydrogen ion-selective electrode, as a working electrode.

As calibration solutions, products of ALKO (Cat. No. A701-001, A701-002, A701-003) were used, having determined concentrations of specific ion species, a plasma sample was purchased from NISSUI. A blood analyzer, such as that manufactured by NOVA, identified as Stat Profile Ultra M, determined the ion concentration for mixed ion species-containing calibration solutions, and various ions in serum. FIG. 12a showed is a diagram showing the dynamic sensitivity of a potassium ion electrode and FIG. 12b of a hydrogen electrode. The results are given in Table 1, below.

TABLE 1

Sensitivity for Potassium and Hydrogen Ions

| potentiometric sensor | K+ Level [mM] | | | | H+ [pH] | | | |
|---|---|---|---|---|---|---|---|---|
| | Control 1 | Control 2 | Control 3 | Serum | Control 1 | Control 2 | Control 2 | Serum |
| Experimental value | 2.4 | 4.42 | 6.99 | 4.49 | 7.20 | 7.43 | 7.63 | 7.90 |
| NOVA Blood Analyzer | 2 | 4.3 | 6.8 | 4.5 | 7.19 | 7.44 | 7.65 | 7.90 |
| Sample Standard Value | 2.1 (±0.5) | 4.4 (±0.5) | 7.0 (±0.5) | 4.47 (±0.16) | 7.174 (±0.03) | 7.41 (±0.03) | 7.63 (±0.03) | — |

As seen in the above table 1, the result was accordance with the value of commercially usable NOVA analyzer and sample standard value.

EXPERIMENTAL EXAMPLE 8

Determination Ion Concentration of Unknown Sample using Double Layered Solid-State Reference Electrode Equipped with the Polymeric Reference Electrode Membrane Comprising the Hydrophilic Plasticizer and the Lipophilic Polymer As a reference electrode using the double layered or the mono-layered solid-state reference electrode, which each was equipped with the polymeric reference electrode membrane comprising the hydrophilic plasticizer and the lipophilic polymer, unknown solutions were determined to ion concentration and its precision as follows.

Products of Radiometer (Cat. No. S1585 and S1595) were used as calibration solutions while products of ALKO (Cat. No. A701-001, A701-002, A701-003) were used as control samples having known concentrations of specific ion species. A plasma sample for quality assurance was purchased from NISSUI. For comparison, a blood analyzer, such as that manufactured by NOVA, identified as Stat Profile Ultra M, was used for the measurement of ion concentrations of samples.

Figure 13A:
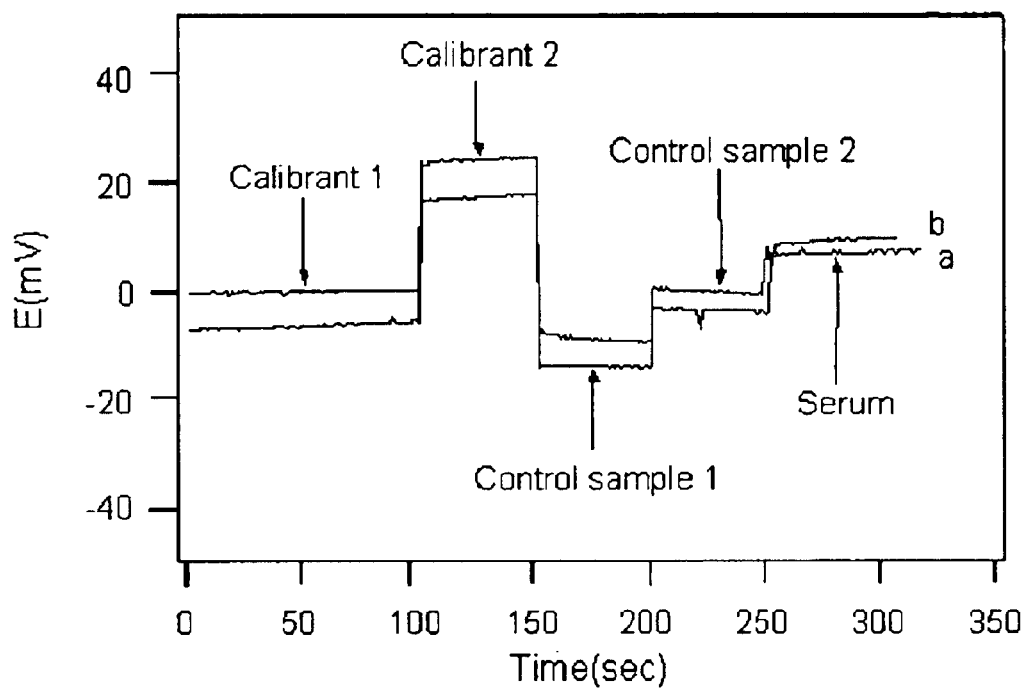
FIG. 13a is a diagram showing the dynamic sensitivity for hydrogen ion in unknown samples, measured by potentiometric sensor comprising; a) a working electrode of a potassium ion-selective electrode and b) a reference electrode of a double layered solid-state reference electrode equipped with a polymeric reference electrode membrane comprising a hydrophilic plasticizer and a lipophilic polymer.
Figure 13B:
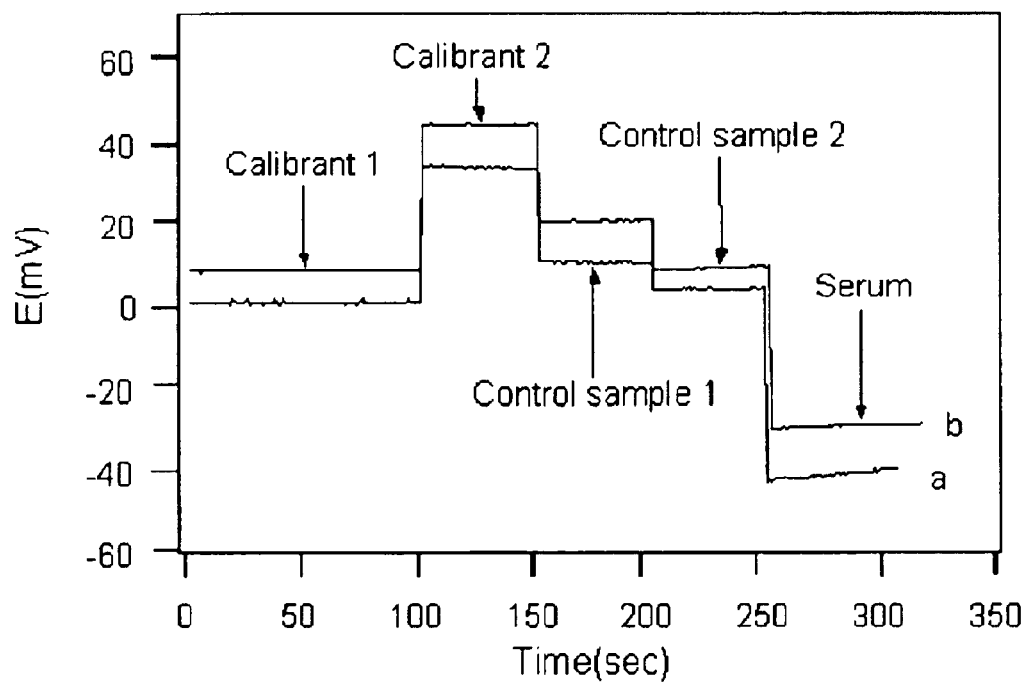
FIG. 13b is a diagram showing the dynamic sensitivity for hydrogen ion in unknown samples, measured by potentiometric sensor comprising the same reference electrode as in the above FIG. 13a, and a hydrogen ion-selective electrode, as a working electrode.

For potassium ions in FIG. 13a and hydrogen ions in FIG. 13b, there are shown a dynamic sensitivity using the same electrode system as above in the experimental example 7, except that, as a reference electrode using the double layered solid-state reference electrode prepared as in the above example 7 in a (a) or a mono-layered solid-state reference electrode prepared as in the above example 8 (b) in the figure.

Summarized in Table 2, below, are measurements, detected by potassium and hydrogen sensors using the reference electrodes of the present invention and a commercially available NOVA blood analyzer, for concentrations of potassium ions and hydrogen ions in samples.

TABLE 2

Sensitivity for Potassium and Hydrogen Ions

| potentiometric sensor | K+ Level [mM] | | | H+ [pH] | | |
|---|---|---|---|---|---|---|
| | Control 1 | Control 2 | Serum | Control 1 | Control 2 | Serum |
| A | 2.8 | 4.0 | 6.6 | 7.20 | 7.38 | 8.00 |
| B | 2.9 | 4.3 | 6.5 | 7.20 | 7.39 | 7.90 |

TABLE 2-continued

Sensitivity for Potassium and Hydrogen Ions

| potentiometric sensor | K+ Level [mM] | | | H+ [pH] | | |
|---|---|---|---|---|---|---|
| | Control 1 | Control 2 | Serum | Control 1 | Control 2 | Serum |
| NOVA Blood Analyzer | 2.7 | 4.2 | 6.6 | 7.20 | 7.40 | 7.90 |
| Sample Standard Value | 2.7 (±0.5) | 4.3 (±0.5) | — | 7.17 (±0.03) | 7.39 (±0.03) | — | a. Reference electrode prepared as in Example 7
b. Reference electrode prepared as in Example 8

When being introduced to a potassium ion-selective electrode and a hydrogen ion-selective electrode, as seen in Table 2, the double layered reference electrode and the mono-layered reference electrode of the present invention were found to ensure high sensitivity for the ion species as assayed by a commercially available NOVA blood analyzer in current use in hospitals. Their measurements closely agreed with standard values of samples, as well.

The double layered or the mono-layered solid-state reference electrode equipped with the polymeric reference electrode membrane of the present invention can maintain stable potentials to main ion species in blood sample and aqueous solutions, for example, sodium, potassium, calcium, salicylate, chloride and hydrogen ions, for a long period of time in broad concentration ranges, and also to mixed ion species-containing calibration solutions, serum and whole bloods. Additionally, the reference electrode can be rapidly activated within several seconds, and can reproduce measurements with consistency. Further, the solid-state reference electrodes of the present invention can introduce to a miniaturized multi-potentiometric sensor, which is additionally contained at least one ion-selective electrode as the working electrode and thus is highly reliable.

As described hereinbefore, the polymeric reference electrode membrane of the present invention comprises (a) one selected from the porous polymer or the hydrophilic plasticizer and (b) the lipophilic polymer. Optionally, the polymeric membrane may further comprise the adhesion-enhancing material. Such the reference electrode equipped with polymeric reference electrode membrane has excellent adhesion and thus has extended lifetime for storage and use. In addition, the solid-state reference electrode can reproduce measurements with consistency, and be stabile to mixed ion species, protein-containing serum and whole bloods, thereby showing high reliability. Therefore, a miniaturized multi-potentiometric sensor can be fabricated comprising one of the solid-state reference electrodes of the present invention and the working electrode of a set of ion-selective electrodes, and can be applied to various fields, such as clinical analysis, environmental analysis, food analysis and industrial specimen analysis.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A reference electrode comprising:
    a polymeric reference electrode membrane comprising (a) one selected from a cellulose based porous polymer and a hydrophilic plasticizer and (b) a lipophilic polymer, wherein the hydrophilic plasticizer is selected from the group consisting of glycerol, polyethylene glycol, ethylene glycol monomethyl ether, ethylene glycol, formamide and a combination thereof;
    an inner reference electrode 3 positioned at the center within the reference electrode; and
    an inner reference electrolyte 7 filling the internal space of the reference electrode;
    wherein the polymeric reference electrode membrane 8 is mounted to an end of the electrode,
    wherein the inner reference electrolyte 7 is a hydrogel obtained by dissolving 1–15% by weight of a hydrophilic polymer in 0.01–3.0 M aqueous solution saturated with a salt selected from the group consisting of KCl, NaCl, KNO3 and NH4NO3, each of which is similar in mobility.

2. The electrode as set forth in claim 1, wherein the polymeric reference electrode membrane 8 comprises a porous polymer and a lipophilic polymer, and the inner reference electrode 3 is made of silver/silver chloride.

3. The electrode as set forth in claim 1, wherein the polymeric reference electrode membrane 8 comprises a hydrophilic plasticizer and a lipophilic polymer, and the inner reference electrode 3 is made of silver/silver chloride.

4. The electrode as set forth in claim 1, wherein the hydrophilic polymer is selected from the group consisting of polyvinylpyrrolidone, polyvinyl alcohol, poly (methyl methacrylate), agar, gelatin.

5. The reference electrode as set forth in claim 1, wherein the lipophilic polymer is selected from the group consisting of silicone rubber, poly (vinyl chloride), polyurethane, poly (vinyl chloride) carboxylated copolymer, poly (vinyl chloride-co-vinyl acetate-co-vinyl alcohol) and a combination thereof.

6. The reference electrode as set forth in claim 1, wherein the polymeric reference electrode membrane comprises 5–70% by weight of the porous polymer and 30–95% by weight of the lipophilic polymer.

7. The membrane as set forth in claim 1, wherein the polymeric reference electrode membrane comprises 10–50% by weight of the porous polymer and 50–90% by weight of the lipophilic polymer.

8. The membrane as set forth in claim 1, wherein the polymeric reference electrode membrane comprises 20–70% by weight of the hydrophilic plasticizer and 30–80% by weight of the lipophilic polymer.

9. The membrane as set forth in claim 1, wherein the polymeric reference electrode membrane further contains an adhesion-enhancing material at an amount of 0.001–1.0% by weight on the total weight of composition.

10. The reference electrode as set forth in claim 9, wherein the adhesion-enhancing material is a highly reactive silicon compound selected from the group consisting of diluted silicon tetrachloride ($SiCl_4$), aminopropyltriethoxy silane, N-[3(trimethoxysilyl)propyl]ethylenediamine, N(2-aminoethyl)-3-aminopropyltrimethoxy silane, 3-methacryloxypropyltrimethoxy silane, N-(2-vinylbenzylamino)ethyl)-3-aminopropyl trimethoxysilane, 3-glycidoxypropyltrimethoxy silane, methyltrimethoxy silane and phenyltrimethoxy silane.

11. A solid-state reference electrode comprising:
    a) a substrate 10;
    b) an insulating film layer 9 formed on the substrate;
    c) a reference electrode material 11 insulated by the insulating film layer 9; and
    d) a polymeric reference electrode membrane 8 protecting the reference electrode material 11, wherein the polymeric reference electrode membrane comprises (a) one selected from a cellulose based porous polymer and a hydrophilic plasticizer and (b) a lipophilic polymer, the hydrophilic plasticizer being selected from the group consisting of glycerol, polyethylene glycol, ethylene glycol monomethyl ether, ethylene glycol, formamide and a combination thereof,
    wherein the polymeric reference electrode membrane 8 is additionally fixed to a hydrogel layer 12, thereby the reference electrode material 11 is protected by the polymeric reference electrode membrane and the hydrogel layer and is made of silver/silver chloride 19.

12. The electrode as set forth in claim 11, wherein the polymeric reference electrode membrane is a mono-layer polymeric reference electrode membrane 13 comprising a hydrophilic plasticizer and a lipophilic polymer, and covers the reference electrode material 11, thereby the reference electrode material 11 is protected by the mono-layer and is made of silver/silver chloride.

13. A The electrode as set forth in claim 12, wherein the mono-layer polymeric reference electrode membrane 13 comprises 20–70% by weight of a hydrophilic plasticizer saturated with a salt selected from the group consisting of KCl, NaCl, $KNO_3$ and $NH_4NO_3$ and 30–80% by weight of a lipophilic polymer.

14. The electrode as set forth in claim 11, wherein the substrate 10 is made of a material selected from the group consisting of alumina-containing ceramics, silicon, poly (vinyl chloride), polyester, polycarbonate and semiconductor materials.

15. The electrode as set forth in claim 11, wherein the hydrogel layer 12 is prepared by dissolving a hydrophilic polymer at an amount of 1–15% by weight in a 0.01–3.0 M aqueous solution saturated with a salt selected from the group consisting of KCl, NaCl, $KNO_3$ and $NH_4NO_3$, each of which is similar in mobility.

16. The electrode as set forth in claim 15, wherein the hydrophilic polymer is selected from the group consisting of polyvinylpyrrolidone, polyvinyl alcohol, poly(methyl methacrylate), agar, gelatin and mixtures thereof.

17. A potentiometric sensor comprising the solid-state reference electrode of claim 11 and a working electrode comprising ion-selective electrodes.

18. The reference electrode as set forth in claim 1, wherein the porous polymer is selected from the group consisting of cellulose acetate, cellulose acetate butylate, cellulose triacetate, nitro cellulose and a combination thereof.

19. The solid-state reference electrode as set forth in claim 11, wherein the porous polymer is selected from the group consisting of cellulose acetate, cellulose acetate butylate, cellulose triacetate, nitro cellulose and a combination thereof.

20. The solid-state reference electrode as set forth in claim 11, wherein the lipophilic polymer is selected from the group consisting of silicone rubber, poly (vinyl chloride), polyurethane, poly (vinyl chloride) carboxylated copolymer, poly (vinyl chloride-co-vinyl acetate-co-vinyl alcohol) and a combination thereof.

21. The solid-state reference electrode as set forth in claim 11, wherein the polymeric reference electrode membrane comprises 5–70% by weight of the porous polymer and 30–95% by weight of the lipophilic polymer.

22. The solid-state reference electrode as set forth in claim 11, wherein the polymeric reference electrode membrane comprises 10–50% by weight of the porous polymer and 50–90% by weight of the liphophilic polymer.

23. The solid-state reference electrode as set forth in claim 11, wherein the polymeric reference electrode membrane comprises 20–70% by weight of the hydrophilic plasticizer and 30–80% by weight of the lipophilic polymer.

24. The solid-state reference electrode as set forth in claim 11, wherein the polymeric reference electrode membrane further contains an adhesion-enhancing material at an amount of 0.001–1.0% by weight on the total weight of composition.

25. The solid-state reference electrode as set forth in claim 24, wherein the adhesion-enhancing material is a highly reactive silicon compound selected from the group consisting of diluted silicon tetrachloride ($SiCl_4$), aminopropyltriethoxy silane, N-[3(trimethoxysilyl) propyl] ethylenediamine, N(2-aminoethyl)-3-aminopropyltrimethoxy silane, 3-methacryloxypropyltrimethoxy silane, N-(2-vinylbenzylamino)ethyl)-3-aminopropyl trimethoxysilane, 3-glycidoxypropyltrimethoxy silane, methyltrimethoxy silane and phenyltrimethoxy silane.

* * * * *